(12) United States Patent
Sheppard

(10) Patent No.: US 6,803,450 B2
(45) Date of Patent: *Oct. 12, 2004

(54) ADIPOCYTE-SPECIFIC PROTEIN HOMOLOGS

(75) Inventor: Paul O. Sheppard, Granite Falls, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/392,706
(22) Filed: Mar. 20, 2003
(65) Prior Publication Data
US 2003/0176659 A1 Sep. 18, 2003

Related U.S. Application Data

(63) Continuation of application No. 09/506,852, filed on Feb. 17, 2000, now Pat. No. 6,566,499, which is a continuation-in-part of application No. 09/118,408, filed on Jul. 17, 1998, now Pat. No. 6,265,544.
(60) Provisional application No. 60/053,154, filed on Jul. 18, 1997, now abandoned.

(51) Int. Cl.[7] .................. C07K 17/00; C07H 21/04; C12N 1/20; C12N 5/00; C12P 21/06
(52) U.S. Cl. .............. 530/350; 536/23.1; 435/252.3; 435/325; 435/320.1; 435/69.1
(58) Field of Search .............. 530/350; 536/23.1; 435/252.3, 325, 320.1, 69.1

(56) References Cited

U.S. PATENT DOCUMENTS

| 6,265,544 B1 | 7/2001 | Sheppard | 530/350 |
|---|---|---|---|
| 6,566,499 B1 | 5/2003 | Sheppard | 530/350 |

FOREIGN PATENT DOCUMENTS

| EP | 679 716 | 11/1995 |
|---|---|---|
| WO | 96/39429 | 12/1996 |
| WO | 99/28462 | 6/1999 |

OTHER PUBLICATIONS

Bork , Genome Research, 10:398–400, 2000.*
Van de Loo et al. , Proc. Natl. Acad. Sci. 92:6743–6747, 1995.*
Broun et al. , Science 282:1315–1317, 1998.*
Kerlavage, TIGR EST, 1997, Accession No. AA368885.
Marra et al., The WASH U–HHMI Mouse EST Project, 1997, Accession No. AA032996.
Nakano et al., J. Biochem. 120: 803–812, 1996.
Lee et al., PNAS 92: 8303–8307, 1995, Accession No. H35826.
Lee et al., PNAS 92: 8303–8307, 1995, Accession No. H34998.
Lee et al., PNAS 92: 8303–8307, 1995, Accession No. AA686347.
Lee et al., PNAS 92: 8303–8307, 1995, Accession No. AA686346.
Lee et al., PNAS 92: 8303–8307, 1995, Accession No. AA686317.
Kerlavage, TIGR EST, 1997, Accession No. AA368885.
Kerlavage, TIGR EST, 1997, Accession No. AA303716.
Human STS SHGC–11286, 1995, Accession No. G11441.
Wilson, WASH U–Merck EST Project, 1995, Accession No. Accession No. W80541.
Wilson, WASH U–Merck EST Project, 1995, Accession No. W38610.
Wilson, WASH U–Merck EST Project, 1995, Accession No. N90896.
Wilson, WASH U–Merck EST Project, 1995, Accession No. W92457.
Wilson, WASH U–Merck EST Project, 1995, Accession No. H83155.
Wilson, WASH U–Merck EST Project, 1995 Accession No. T46871.
Wilson, WASH U–Merck EST Project, 1995, Accession No. T51153.
Wilson, WASH U–Merck EST Project, 1995, Accession No. R06067.
Wilson, WASH U–Merck EST Project, 1995, Accession No. R06169.
Wilson, WASH U–Merck EST Project, 1995, Accession No. R31097.
Wilson, WASH U–Merck EST Project, 1995, Accession No. R31145.
Wilson, WASH U–Merck EST Project, 1995, Accession No. R70938.
Wilson, WASH U–Merck EST Project, 1995, Accession No. R70990.
Wilson, WASH U–Merck EST Project, 1995, Accession No. R69486.
Wilson, WASH U–Merck EST Project, 1995, Accession No. R96189.
Wilson, WASH U–Merck EST Project, 1995, Accession No. H58515.
LIFE SEQ™ Clone Information Results, Incyte Pharmaceuticals, Inc., 1995, Accession No. INC606132.
LIFE SEQ™ Clone Information Results, Incyte Pharmaceuticals, Inc., 1995, Accession No. INC354384.
LIFE SEQ™ Clone Information Results, Incyte Pharmaceuticals, Inc., 1995, Accession No. INC354999.

(List continued on next page.)

Primary Examiner—Rebecca E. Prouty
Assistant Examiner—Delia Ramirez
(74) Attorney, Agent, or Firm—Brian J. Walsh

(57) ABSTRACT

The present invention relates to polynucleotide and polypeptide molecules for zsig37, a novel member of the family of proteins bearing a collagen-like domain and a globular domain. The polypeptides, and polynucleotides encoding them, are involved in dimerization or oligomerization and may be used in the study thereof. The present invention also includes antibodies to the zsig37 polypeptides.

24 Claims, 2 Drawing Sheets-

OTHER PUBLICATIONS

LIFE SEQ™ Clone Information Results, Incyte Pharmaceuticals, Inc., 1995, Accession No. INC214678.
LIFE SEQ™ Clone Information Results, Incyte Pharmaceuticals, Inc., 1995, Accession No. INC366750.
LIFE SEQ™ Clone Information Results, Incyte Pharmaceuticals, Inc., 1995, Accession No. INC359154.
LIFE SEQ™ Clone Information Results, Incyte Pharmaceuticals, Inc., 1995, Accession No. INC136632.
LIFE SEQ™ Clone Information Results, Incyte Pharmaceuticals, Inc., 1995, Accession No. INC115373.
LIFE SEQ™ Clone Information Results, Incyte Pharmaceuticals, Inc., 1995, Accession No. INC275341.
LIFE SEQ™ Clone Information Results, Incyte Pharmaceuticals, Inc., 1995, Accession No. INC589727.
LIFE SEQ™ Library Information Results, Incyte Pharmaceuticals, Inc., 1995, Accession No. BRTTUT01.
LIFE SEQ™ Library Information Results, Incyte Pharmaceuticals, Inc., 1995, Accession No. RATRNOT01.
LIFE SEQ™ Library Information Results, Incyte Pharmaceuticals, Inc., 1995, Accession No. STOMNOT01.
LIFE SEQ™ Library Information Results, Incyte Pharmaceuticals, Inc., 1995, Accession No. SYNORAT01.
LIFE SEQ™ Library Information Results, Incyte Pharmaceuticals, Inc., 1995, Accession No. SYNORAB01.
LIFE SEQ™ Library Information Results, Incyte Pharmaceuticals, Inc., 1995, Accession No. TESTNOT01.
LIFE SEQ™ Library Information Results, Incyte Pharmaceuticals, Inc., 1995, TESTNOT03.
LIFE SEQ™ Library Information Results, Incyte Pharmaceuticals, Inc., 1995, Accession No. UTRSNOT01.
Matsubara and Okubo, Human Gene Signature HUMG SO 3849, WO 95/14772–A1, 1998, Acc. No. T22277.
Fujiwara et al., Otsuka cDNA Project, 1996, Accession No. C18241.
Fujiwara et al., Otsuka cDNA Project, 1996, Accession No. C18539.
Fujiwara et al., Otsuka cDNA Project, 1996, Accession No. C00999.
Fujiwara et al., Otsuka cDNA Project, 1996, Accession No. C18539.
Marra et al., WASH U HHM/Mouse EST Project, 1996, Accession No. D18462.
Marra et al., WASH U HHM/Mouse EST Project, 1996, Accession No. AA032996.
Marra et al., WASH U HHM/Mouse EST Project, 1996, Accession No. AA036370.
Marra et al., WASH U HHM/Mouse EST Project, 1996, Accession No. AA275775.
Marra et al., WASH U HHM/Mouse EST Project, 1996, Accession No. AA792482.
Marra et al., WASH U HHM/Mouse EST Project, 1996, Accession No. AA049854.
Marra et al., WASH U HHM/Mouse EST Project, 1996, Accession No. AA611092.
LIFE SEQ™ Clone Information Results, Incyte Pharmaceuticals, Inc., 1996, Accession No. INC2056048.
LIFE SEQ™ Clone Information Results, Incyte Pharmaceuticals, Inc., 1996, Accession No. INC1556127.
LIFE SEQ™ Clone Information Results, Incyte Pharmaceuticals, Inc., 1996, Accession No. INC1519407.
LIFE SEQ™ Clone Information Results, Incyte Pharmaceuticals, Inc., 1996, Accession No. INC1518311.
LIFE SEQ™ Clone Information Results, Incyte Pharmaceuticals, Inc., 1996, Accession No. INC754800.
LIFE SEQ™ Clone Information Results, Incyte Pharmaceuticals, Inc., 1996, Accession No. INC866487.
LIFE SEQ™ Clone Information Results, Incyte Pharmaceuticals, Inc., 1996, Accession No. INC1384906.
LIFE SEQ™ Clone Information Results, Incyte Pharmaceuticals, Inc., 1996, Accession No. INC1213724.
LIFE SEQ™ Clone Information Results, Incyte Pharmaceuticals, Inc., 1996, Accession No. INC1211726.
LIFE SEQ™ Clone Information Results, Incyte Pharmaceuticals, Inc., 1996, Accession No. INC1211936.
LIFE SEQ™ Clone Information Results, Incyte Pharmaceuticals, Inc., 1996, Accession No. INC1968920.
LIFE SEQ™ Clone Information Results, Incyte Pharmaceuticals, Inc., 1996, Accession No. INC1301078.
LIFE SEQ™ Clone Information Results, Incyte Pharmaceuticals, Inc., 1996, Accession No. INC2020629.
LIFE SEQ™ Clone Information Results, Incyte Pharmaceuticals, Inc., 1996, Accession No. INC2019681.
LIFE SEQ™ Clone Information Results, Incyte Pharmaceuticals, Inc., 1996, Accession No. INC1956767.
LIFE SEQ™ Clone Information Results, Incyte Pharmaceuticals, Inc., 1996, Accession No. INC1954880.
LIFE SEQ™ Clone Information Results, Incyte Pharmaceuticals, Inc., 1996, Accession No. INC1841806.
LIFE SEQ™ Clone Information Results, Incyte Pharmaceuticals, Inc., 1996, Accession No. INC1800107.
LIFE SEQ™ Clone Information Results, Incyte Pharmaceuticals, Inc., 1996, Accession No. INC1486178.
LIFE SEQ™ Clone Information Results, Incyte Pharmaceuticals, Inc., 1996, Accession No. INC1402955.
LIFE SEQ™ Clone Information Results, Incyte Pharmaceuticals, Inc., 1996, Accession No. INC1353792.
LIFE SEQ™ Clone Information Results, Incyte Pharmaceuticals, Inc., 1996, Accession No. INC1351682.
LIFE SEQ™ Clone Information Results, Incyte Pharmaceuticals, Inc., 1996, Accession No. INC869429.
LIFE SEQ™ Clone Information Results, Incyte Pharmaceuticals, Inc., 1996, Accession No. INC794320.
LIFE SEQ™ Clone Information Results, Incyte Pharmaceuticals, Inc., 1996, Accession No. INC798218.
LIFE SEQ™ Clone Information Results, Incyte Pharmaceuticals, Inc., 1996, Accession No. INC1454992.
LIFE SEQ™ Clone Information Results, Incyte Pharmaceuticals, Inc., 1996, Accession No. INC1711445.
LIFE SEQ™ Clone Information Results, Incyte Pharmaceuticals, Inc., 1996, Accession No. INC1709564.
LIFE SEQ™ Clone Information Results, Incyte Pharmaceuticals, Inc., 1996, Accession No. INC1818761.
LIFE SEQ™ Clone Information Results, Incyte Pharmaceuticals, Inc., 1996, Accession No. INC945528.
LIFE SEQ™ Clone Information Results, Incyte Pharmaceuticals, Inc., 1996, Accession No. INC722700.
LIFE SEQ™ Clone Information Results, Incyte Pharmaceuticals, Inc., 1996, Accession No. INC711568.
LIFE SEQ™ Clone Information Results, Incyte Pharmaceuticals, Inc., 1996, Accession No. INC2081011.
LIFE SEQ™ Clone Information Results, Incyte Pharmaceuticals, Inc., 1996, Accession No. INC1497965.
LIFE SEQ™ Library Information Results, Incyte Pharmaceuticals, Inc., 1996, Accession No. BEPINOT01.
LIFE SEQ™ Library Information Results, Incyte Pharmaceuticals, Inc., 1996, Accession No. BLADNOT04.

LIFE SEQ™ Library Information Results, Incyte Pharmaceuticals, Inc., 1996, Accession No. BRAITUT02.
LIFE SEQ™ Library Information Results, Incyte Pharmaceuticals, Inc., 1996, Accession No. BRAITUT03.
LIFE SEQ™ Library Information Results, Incyte Pharmaceuticals, Inc., 1996, Accession No. BRAITUT08.
LIFE SEQ™ Library Information Results, Incyte Pharmaceuticals, Inc., 1996, Accession No. BRSTNOT04.
LIFE SEQ™ Library Information Results, Incyte Pharmaceuticals, Inc., 1996, Accession No. BRSTNOT07.
LIFE SEQ™ Library Information Results, Incyte Pharmaceuticals, Inc., 1996, Accession No. CONNNOT01.
LIFE SEQ™ Library Information Results, Incyte Pharmaceuticals, Inc., 1996, Accession No. COLNNOT07.
LIFE SEQ™ Library Information Results, Incyte Pharmaceuticals, Inc., 1996, Accession No. COLNNOT27.
LIFE SEQ™ Library Information Results, Incyte Pharmaceuticals, Inc., 1996, Accession No. LATRTUT02.
LIFE SEQ™ Library Information Results, Incyte Pharmaceuticals, Inc., 1996, Accession No. LUNGAST01.
LIFE SEQ™ Library Information Results, Incyte Pharmaceuticals, Inc., 1996, Accession No. OVARNOT03.
LIFE SEQ™ Library Information Results, Incyte Pharmaceuticals, Inc., 1996, Accession No. PENITUT01.
LIFE SEQ™ Library Information Results, Incyte Pharmaceuticals, Inc., 1996, Accession No. PROSNOT16.
LIFE SEQ™ Library Information Results, Incyte Pharmaceuticals, Inc., 1996, Accession No. PROSNOT20.
LIFE SEQ™ Library Information Results, Incyte Pharmaceuticals, Inc., 1996, Accession No. RATRNOT02.
LIFE SEQ™ Library Information Results, Incyte Pharmaceuticals, Inc., 1996, Accession No. SYNOOAT01.
LIFE SEQ™ Library Information Results, Incyte Pharmaceuticals, Inc., 1996, Accession No. SYNORAT04.
LIFE SEQ™ Library Information Results, Incyte Pharmaceuticals, Inc., 1996, Accession No. UTRSNOT08.
LIFE SEQ™ Library Information Results, Incyte Pharmaceuticals, Inc., 1996, Accession No. SINTBST01.
LIFE SEQ™ Library Information Results, Incyte Pharmaceuticals, Inc., 1996, Accession No. CORPNOT02.
LIFE SEQ™ Library Information Results, Incyte Pharmaceuticals, Inc., 1996, Accession No. BRSTNOT02.
Strausberg, Natl. Canc. Inst. Cancer Genome Anatomy Project, 1997, Accession No. AA631689.
Davies, Human DNA SEQ from Clone #151B14, 1997, Accession No. Z82188.
TIGR Tentative Human Consensus, 1997, Accession No. THC176507.
TIGR Tentative Human Consensus, 1997, Accession No. H83155.
TIGR Tentative Human Consensus, 1997, Accession No. AA150340.
TIGR Tentative Human Consensus, 1997, Accession No. T51153.
TIGR Tentative Human Consensus, 1997, Accession No. N90896.
TIGR Tentative Human Consensus, 1997, Accession No. W38610.
TIGR Tentative Human Consensus, 1997, Accession No. EST80205.
LIFE SEQ™ Clone Information Results, Incyte Pharmaceuticals, Inc., 1997, Accession No. INC3151408.
LIFE SEQ™ Clone Information Results, Incyte Pharmaceuticals, Inc., 1997, Accession No. INC3148085.
LIFE SEQ™ Clone Information Results, Incyte Pharmaceuticals, Inc., 1997, Accession No. INC2102183.
LIFE SEQ™ Clone Information Results, Incyte Pharmaceuticals, Inc., 1997, Accession No. INC2110193.
LIFE SEQ™ Clone Information Results, Incyte Pharmaceuticals, Inc., 1997, Accession No. INC2114819.
LIFE SEQ™ Clone Information Results, Incyte Pharmaceuticals, Inc., 1997, Accession No. INC3242055.
LIFE SEQ™ Clone Information Results, Incyte Pharmaceuticals, Inc., 1997, Accession No. INC2838403.
LIFE SEQ™ Clone Information Results, Incyte Pharmaceuticals, Inc., 1997, Accession No. INC2531692.
LIFE SEQ™ Clone Information Results, Incyte Pharmaceuticals, Inc., 1997, Accession No. INC3327438.
LIFE SEQ™ Clone Information Results, Incyte Pharmaceuticals, Inc., 1997, Accession No. INC3326103.
LIFE SEQ™ Clone Information Results, Incyte Pharmaceuticals, Inc., 1997, Accession No. INC3123349.
LIFE SEQ™ Clone Information Results, Incyte Pharmaceuticals, Inc., 1997, Accession No. INC2798595.
LIFE SEQ™ Clone Information Results, Incyte Pharmaceuticals, Inc., 1997, Accession No. INC2325151.
LIFE SEQ™ Clone Information Results, Incyte Pharmaceuticals, Inc., 1997, Accession No. INC2253332.
LIFE SEQ™ Clone Information Results, Incyte Pharmaceuticals, Inc., 1997, Accession No. INC3208594.
LIFE SEQ™ Clone Information Results, Incyte Pharmaceuticals, Inc., 1997, Accession No. INC3437175.
LIFE SEQ™ Clone Information Results, Incyte Pharmaceuticals, Inc., 1997, Accession No. INC3443225.
LIFE SEQ™ Clone Information Results, Incyte Pharmaceuticals, Inc., 1997, Accession No. INC3146485.
LIFE SEQ™ Clone Information Results, Incyte Pharmaceuticals, Inc., 1997, Accession No. LIN1454992T6.
LIFE SEQ™ Clone Information Results, Incyte Pharmaceuticals, Inc., 1997, Accession No. LIN1454992F6.
LIFE SEQ™ Clone Information Results, Incyte Pharmaceuticals, Inc., 1997, Accession No. INC3345839.
LIFE SEQ™ Clone Information Results, Incyte Pharmaceuticals, Inc., 1997, Accession No. INC2483006.
LIFE SEQ™ Clone Information Results, Incyte Pharmaceuticals, Inc., 1997, Accession No. INC2483840.
LIFE SEQ™ Clone Information Results, Incyte Pharmaceuticals, Inc., 1997, Accession No. INC2482123.
LIFE SEQ™ Clone Information Results, Incyte Pharmaceuticals, Inc., 1997, Accession No. INC2225074.
LIFE SEQ™ Clone Information Results, Incyte Pharmaceuticals, Inc., 1997, Accession No. INC2883977.
LIFE SEQ™ Clone Information Results, Incyte Pharmaceuticals, Inc., 1997, Accession No. INC3218603.
LIFE SEQ™ Clone Information Results, Incyte Pharmaceuticals, Inc., 1997, Accession No. INC2465877.
LIFE SEQ™ Clone Information Results, Incyte Pharmaceuticals, Inc., 1997, Accession No. INC2261326.
LIFE SEQ™ Clone Information Results, Incyte Pharmaceuticals, Inc., 1997, Accession No. INC2612155.
LIFE SEQ™ Clone Information Results, Incyte Pharmaceuticals, Inc., 1997, Accession No. INC2543989.
LIFE SEQ™ Clone Information Results, Incyte Pharmaceuticals, Inc., 1997, Accession No. INC3226494.
LIFE SEQ™ Library Information Results, Incyte Pharmaceuticals, Inc., 1997, Accession No. ADRENON04.
LIFE SEQ™ Library Information Results, Incyte Pharmaceuticals, Inc., 1997, Accession No. COLAUCT01.

LIFE SEQ™ Library Information Results, Incyte Pharmaceuticals, Inc., 1997, Accession No. DRGCNOT.
LIFE SEQ™ Library Information Results, Incyte Pharmaceuticals, Inc., 1997, Accession No. GBLANOT02.
LIFE SEQ™ Library Information Results, Incyte Pharmaceuticals, Inc., 1997, Accession No. HEAONOT04.
LIFE SEQ™ Library Information Results, Incyte Pharmaceuticals, Inc., 1997, Accession No. LNODNOT05.
LIFE SEQ™ Library Information Results, Incyte Pharmaceuticals, Inc., 1997, Accession No. NPOLNOT01.
LIFE SEQ™ Library Information Results, Incyte Pharmaceuticals, Inc., 1997, Accession No. OVARNOT02.
LIFE SEQ™ Library Information Results, Incyte Pharmaceuticals, Inc., 1997, Accession No. PENCNOT03.
LIFE SEQ™ Library Information Results, Incyte Pharmaceuticals, Inc., 1997, Accession No. PENCNOT05.
LIFE SEQ™ Library Information Results, Incyte Pharmaceuticals, Inc., 1997, Accession No. PENGNOT01.
LIFE SEQ™ Library Information Results, Incyte Pharmaceuticals, Inc., 1997, Accession No. PENITUT01.
LIFE SEQ™ Library Information Results, Incyte Pharmaceuticals, Inc., 1997, Accession No. SPLNNOT09.
LIFE SEQ™ Library Information Results, Incyte Pharmaceuticals, Inc., 1997, Accession No. SMCANOT01.
LIFE SEQ™ Library Information Results, Incyte Pharmaceuticals, Inc., 1997, Accession No. SEMVNOT01.
LIFE SEQ™ Library Information Results, Incyte Pharmaceuticals, Inc., 1997, Accession No. SINJNOT02.
LIFE SEQ™ Library Information Results, Incyte Pharmaceuticals, Inc., 1997, Accession No. TESTNOT07.
LIFE SEQ™ Library Information Results, Incyte Pharmaceuticals, Inc., 1997, Accession No. THYRNOT08.
LIFE SEQ™ Library Information Results, Incyte Pharmaceuticals, Inc., 1997, Accession No. UTRSNOT02.
LIFE SEQ™ Library Information Results, Incyte Pharmaceuticals, Inc., 1997, Accession No. UTRSTUT04.
LIFE SEQ™ Library Information Results, Incyte Pharmaceuticals, Inc., 1997, Accession No. UTRSNOT11.
LIFE SEQ™ Library Information Results, Incyte Pharmaceuticals, Inc., 1997, Accession No. OVARTUT01.
LIFE SEQ™ Library Information Results, Incyte Pharmaceuticals, Inc., 1997, Accession No. PENCNOT06.
LIFE SEQ™ Library Information Results, Incyte Pharmaceuticals, Inc., 1997, Accession No. UTRSNOT16.
Sheffield et al., University of Iowa Program for Rat Gene Discovery and Mapping, 1998, Accession No. AA955459.
Sheffield et al., University of Iowa Program for Rat Gene Discovery and Mapping, 1998, Accession No. AA998774.
LIFE SEQ™ Clone Information Results, Incyte Pharmaceuticals, Inc., 1998, Accession No. INC3529224.
LIFE SEQ™ Clone Information Results, Incyte Pharmaceuticals, Inc., 1998, Accession No. INC4760988.
LIFE SEQ™ Clone Information Results, Incyte Pharmaceuticals, Inc., 1998, Accession No. INC3682079.
LIFE SEQ™ Library Information Results, Incyte Pharmaceuticals, Inc., 1998, Accession No. BLADNOT09.
LIFE SEQ™ Library Information Results, Incyte Pharmaceuticals, Inc., 1998, Accession No. BRAMNOT01.
LIFE SEQ™ Library Information Results, Incyte Pharmaceuticals, Inc., 1998, Accession No. LUNGNOT33.
LIFE SEQ™ Clone Information Results, Incyte Pharmaceuticals, Inc., date unknown, Acc. No. FLN1818761CB1.
LIFE SEQ™ Clone Information Results, Incyte Pharmaceuticals, Inc., date unknown, Acc. No. FLN1867810CA2.
LIFE SEQ™ Clone Information Results, Incyte Pharmaceuticals, Inc., date unknown, Acc. No. LIN354999R1.
LIFE SEQ™ Clone Information Results, Incyte Pharmaceuticals, Inc., date unknown, Acc. No. LIN214464F1.
LIFE SEQ™ Clone Information Results, Incyte Pharmaceuticals, Inc., date unknown, Acc. No. LIN354999F1.
LIFE SEQ™ Clone Information Results, Incyte Pharmaceuticals, Inc., date unknown, Acc. No. LIN214464R1.
LIFE SEQ™ Clone Information Results, Incyte Pharmaceuticals, Inc., date unknown, Acc. No. LIN136632F1.
"GIP, a putative GPCR interacting protein," GenBank Acc. No. O9GZR4, Mar. 2001.

* cited by examiner

```
zsig37_3_z  MGSRGQGLLLAYCLLLAFASG-------------------------- ; 21
HUMUPST2_1  MLLLGAVLLLLALP--------------------------------- ; 14
C1QA_HUMAN  MEGPRGWLVLCVLAISLA------------------------------ ; 18
HP25_TAMAS  MPAQRGGALSMGAAGFWILVLSITSALA-------------------- ; 28
HP27_TAMAS  MYEAGKRASFMGGAGIWILALSVLMHVVCS------------------ ; 30
CERL_RAT    MPAPGRGPRGPLLSMPGRRGALREPADFGSSLGAALALLLLLLPACC ; 47 zsig37_3_z  -----LVLSRVPHVQGEQQEWEGTEELPSPPDHAERAEEQHEKYRPS ; 63
HUMUPST2_1  -----GHDQ--------------ETTTQGP----------GVLLPL ; 31
C1QA_HUMAN  -----SMVT--------------EDLCRAPD------------GK ; 32
HP25_TAMAS  -----DSNNQGNSEPC------------------------------- ; 39
HP27_TAMAS  -------ETQGNPESC------------------------------- ; 39
CERL_RAT    PVKA-QNDTEPIVLEGKC----LVVCDSSPSGDGAVTSSL------- ; 82 zsig37_3_z  QDQGLPASRCLRCCDPGTSMYPATAVPQINITILKGEKGDRGDRGLQ ; 110
HUMUPST2_1  PKGACTGWMAGIPGHPGHNGAPGRDG-RDGTPGEKGEKGDPGLIGPK ; 77
C1QA_HUMAN  KGEAGRPGRRGRPGLKGEQGEPGAPGIRTGIQGLKGDQGEPGPSGNP ; 79
HP25_TAMAS  --------------------------------GPPGPPGPPGIP ; 51
HP27_TAMAS  --------------------------------NVPGPQGPPGMR ; 51
CERL_RAT    --------------------- --------------------- ; 82 zsig37_3_z  GKYGKTGSAGARGHTGPKGQKGSMGAPGE--RCK-SHYAAFSVGRKK ; 154
HUMUPST2_1  GDIGETGVPGAEGPRGFPGIQGRKGEPGE--GAY-VYRSAFSVGLET ; 121
C1QA_HUMAN  GKVGYPGPSGPLGARGIPGIKGTKGSPGN--IKD-QPRPAFSAIRRN ; 123
HP25_TAMAS  GFPGAPGALGPPGPPGVPGIPGPQGPPGDVEKCSSRPKSAFAVKLSE ; 98
HP27_TAMAS  GPPGTPGKPGPPGWNGFPGLPGPPGPPGMTVNCHSKGTSAFAVKANE ; 98
CERL_RAT    --------------------GISVRSG----SAKVAFSATRSTNHE ; 104 zsig37_3_z  PMHSNHYYQTVIFDTEFVNLYDHFNMFTGKFYCYVPGLYFFSLNV-H ; 200
HUMUPST2_1  YVTI--PNMPIRFTKIFYNQQNHYDGSTGKFHCNIPGLYYFAYHI-T ; 165
C1QA_HUMAN  PPMG---GNVVIFDTVITNQEEPYQNHSGRFVCTVPGYYYFTFQV-L ; 166
HP25_TAMAS  RPPE--PFQPIVFKEALYNQEGHFNMATGEFSCVLPGVYNFGFDIRL ; 143
HP27_TAMAS  LPPA--PSQPVIFKEALHDAQGHFDLATGVFTCPVPGLYQFGFHIEA ; 143
CERL_RAT    PSEMSNRTMTIYFDQVLVNIGNHFDLASSIFVAPRKGIYSFSFHVVK ; 151 zsig37_3_z  T---WNQKETYLHIMKNEEEVVILFAQVGDRSIMQSQS--LMLELRE ; 242
HUMUPST2_1  V----YMKDVKVSLFKKDKAMLFTYDQYQENNVDQASG-SVLLHLEV ; 207
C1QA_HUMAN  SQ--WEICLSIVSSSRGQVRRSLGFCDTTNKGLFQVVSGGMVLQLQQ ; 211
HP25_TAMAS  FQ--SSVKIRLMRDGI-QVREK----EAQANDSYKHAMGSVIMALGK ; 183
HP27_TAMAS  VQ--RAVKVSLMRNGT-QVMER----EAEAQDGYEHISGTAILQLGM ; 183
CERL_RAT    VYNRQTIQVSLMQNGY-PVISA----FAGDQDVTREAASNGVLLL-M ; 192 zsig37_3_z  QDQVWVRLYKG-ERENAIFSEELDTYITFSGYLVKHATEP ; 281
HUMUPST2_1  GDQVWLQVYGEGERNGLYADNDNDS--TFTGFLLYHDTN- ; 244
C1QA_HUMAN  GDQVWVEKDP--KKGHIYQGSEADS--VFSGFLIFPSA-- ; 245
HP25_TAMAS  GDKVWLESKL--KGTESEKGI-THI--VFFGYLLYGK--- ; 215
HP27_TAMAS  EDRVWLENKL--SQTDLERGT-VQA--VFSGFLIHEN--- ; 215
CERL_RAT    EREDKVHLKL--ERGNLMGGW-KYS--TFSGFLVFPL--- ; 224
```

Fig. 1

|           | zsig37 | HUMUPST2_1 | C1QA_HUMAN | HP25_TAMAS | HP27_TAMAS | CERL-RAT |
|-----------|--------|------------|------------|------------|------------|----------|
| zsig37    | 100    |            |            |            |            |          |
| HUMUPST2_1| 32     | 100        |            |            |            |          |
| C1QA_HUMAN| 30     | 33         | 100        |            |            |          |
| HP25_TAMAS| 31     | 31         | 32         | 100        |            |          |
| HP27_TAMAS| 28     | 29         | 32         | 53         | 100        |          |
| CERL-RAT  | 21     | 25         | 24         | 27         | 33         | 100      |

Fig. 2

SEQUENCE LISTING

<160> NUMBER OF SEQ ID NOS: 44

<210> SEQ ID NO 1
<211> LENGTH: 2769
<212> TYPE: DNA
<213> ORGANISM: Homo sapien
<220> FEATURE:
<221> NAME/KEY: CDS
<222> LOCATION: (171)...(1013)

<400> SEQUENCE: 1

```
gaattcgaat tcctttgttt ccactgggac ggaatcggag ctctggaggc tgggctggcc      60
aagcgccccg aaggcccgat gcctgacggc tcatgcggcc tccttgtttg cagggcctgg     120
gcaaaaattt acactgagtc ccactcttcg ctccagggcc ggcaggaag atg ggc         176
                                                     Met Gly
                                                       1 tcc cgt gga cag gga ctc ttg ctg gcg tac tgc ctg ctc ctt gcc ttt       224
Ser Arg Gly Gln Gly Leu Leu Leu Ala Tyr Cys Leu Leu Leu Ala Phe
          5                  10                  15 gcc tct ggc ctg gtc ctg agt cgc gtg ccc cat gtc cag ggg gaa cag       272
Ala Ser Gly Leu Val Leu Ser Arg Val Pro His Val Gln Gly Glu Gln
     20                  25                  30 cag gag tgg gag ggg act gag gag ctg ccg tcc cct ccg gac cat gcc       320
Gln Glu Trp Glu Gly Thr Glu Glu Leu Pro Ser Pro Pro Asp His Ala
 35                  40                  45                  50 gag agg gct gaa gaa caa cat gaa aaa tac agg ccc agt cag gac cag       368
Glu Arg Ala Glu Glu Gln His Glu Lys Tyr Arg Pro Ser Gln Asp Gln
                 55                  60                  65 ggg ctc cct gct tcc cgg tgc ttg cgc tgc tgt gac cct ggt acc tcc       416
Gly Leu Pro Ala Ser Arg Cys Leu Arg Cys Cys Asp Pro Gly Thr Ser
             70                  75                  80 atg tac ccg gcg acc gcc gtg ccc cag atc aac atc act atc ttg aaa       464
Met Tyr Pro Ala Thr Ala Val Pro Gln Ile Asn Ile Thr Ile Leu Lys
         85                  90                  95 ggg gag aag ggt gac cgc gga gat cga ggc ctc caa ggg aaa tat ggc       512
Gly Glu Lys Gly Asp Arg Gly Asp Arg Gly Leu Gln Gly Lys Tyr Gly
    100                 105                 110 aaa aca ggc tca gca ggg gcc agg ggc cac act gga ccc aaa ggg cag       560
Lys Thr Gly Ser Ala Gly Ala Arg Gly His Thr Gly Pro Lys Gly Gln
115                 120                 125                 130 aag ggc tcc atg ggg gcc cct ggg gag cgg tgc aag agc cac tac gcc       608
Lys Gly Ser Met Gly Ala Pro Gly Glu Arg Cys Lys Ser His Tyr Ala
                135                 140                 145 gcc ttt tcg gtg ggc cgg aag aag ccc atg cac agc aac cac tac tac       656
Ala Phe Ser Val Gly Arg Lys Lys Pro Met His Ser Asn His Tyr Tyr
            150                 155                 160 cag acg gtg atc ttc gac acg gag ttc gtg aac ctc tac gac cac ttc       704
Gln Thr Val Ile Phe Asp Thr Glu Phe Val Asn Leu Tyr Asp His Phe
        165                 170                 175 aac atg ttc acc ggc aag ttc tac tgc tac gtg ccc ggc ctc tac ttc       752
Asn Met Phe Thr Gly Lys Phe Tyr Cys Tyr Val Pro Gly Leu Tyr Phe
    180                 185                 190 ttc agc ctc aac gtg cac acc tgg aac cag aag gag acc tac ctg cac       800
Phe Ser Leu Asn Val His Thr Trp Asn Gln Lys Glu Thr Tyr Leu His
195                 200                 205                 210 atc atg aag aac gag gag gag gtg gtg atc ttg ttc gcg cag gtg ggc       848
Ile Met Lys Asn Glu Glu Glu Val Val Ile Leu Phe Ala Gln Val Gly
                215                 220                 225
```

-continued

| | | | | | | | | | | | | | | | | |
|---|---|---|---|---|---|---|---|---|---|---|---|---|---|---|---|---|
| gac | cgc | agc | atc | atg | caa | agc | cag | agc | ctg | atg | ctg | gag | ctg | cga | gag | 896 |
| Asp | Arg | Ser | Ile | Met | Gln | Ser | Gln | Ser | Leu | Met | Leu | Glu | Leu | Arg | Glu | |
| | | | 230 | | | | | 235 | | | | | 240 | | | |
| cag | gac | cag | gtg | tgg | gta | cgc | ctc | tac | aag | ggc | gaa | cgt | gag | aac | gcc | 944 |
| Gln | Asp | Gln | Val | Trp | Val | Arg | Leu | Tyr | Lys | Gly | Glu | Arg | Glu | Asn | Ala | |
| | | 245 | | | | | 250 | | | | | 255 | | | | |
| atc | ttc | agc | gag | gag | ctg | gac | acc | tac | atc | acc | ttc | agt | ggc | tac | ctg | 992 |
| Ile | Phe | Ser | Glu | Glu | Leu | Asp | Thr | Tyr | Ile | Thr | Phe | Ser | Gly | Tyr | Leu | |
| | | 260 | | | | | 265 | | | | | 270 | | | | |

| | | | | | | |
|---|---|---|---|---|---|---|
| gtc | aag | cac | gcc | acc | gag | ccc tagctggccg gccacctcct ttcctctcgc | 1043 |
| Val | Lys | His | Ala | Thr | Glu | Pro | |
| 275 | | | | | 280 | | |

| | |
|---|---|
| caccttccac ccctgcgctg tgctgacccc agggctcagc accaggctga ccccaccgcc | 1103 |
| tcttccccga tccctggact ccgactccct ggctttggca ttcagtgaga cgccctgcac | 1163 |
| acacagaaag ccaaagcgat cggtgctccc agatcccgca gcctctggag agagctgacg | 1223 |
| gcagatgaaa tcaccagggc ggggcacccg cgagaaccct ctgggacctt ccgcggccct | 1283 |
| ctctgcacac atcctcaagt gaccccgcac ggcgagacgc gggtggcggc agggcgtccc | 1343 |
| agggtgcggc accgcggctc cagtccttgg aaataattag gcaaattcta aaggtctcaa | 1403 |
| aaggagcaaa gtaaaccgtg gaggacaaag aaaagggttg ttattttttgt ctttccagcc | 1463 |
| agcctgctgg ctcccaagag agaggccttt tcagttgaga ctctgcttaa gagaagatcc | 1523 |
| aaagttaaag ctctggggtc aggggagggg ccggggggcag gaaactacct ctggcttaat | 1583 |
| tcttttaagc cacgtaggaa cttttcttgag ggataggtgg accctgacat ccctgtggcc | 1643 |
| tgcccaagg gctctgctgg tctttctgag tcacagctgc gaggtgatgg gggctggggc | 1703 |
| cccaggcgtc agcctcccag agggacagct gagcccctg ccttggctcc aggttggtag | 1763 |
| aagcagccga agggctcctg acagtggcca gggacccctg ggtcccccag gcctgcagat | 1823 |
| gtttctatga ggggcagagc tcctggtaca tccatgtgtg gctctgctcc accctgtgc | 1883 |
| caccccagag ccctgggggg tggtctccat gcctgccacc ctggcatcgg cttttctgtgc | 1943 |
| cgcctcccac acaaatcagc cccagaaggc cccggggctt tggcttctgt ttttttataaa | 2003 |
| acacctcaag cagcactgca gtctcccatc tcctcgtggg ctaagcatca ccgcttccac | 2063 |
| gtgtgttgtg ttggttggca gcaaggctga tccagacccc ttctgccccc actgccctca | 2123 |
| tccaggcctc tgaccagtag cctgagaggg gcttttttcta ggcttcagag caggggagag | 2183 |
| ctggaagggg ctagaaagct cccgcttgtc tgtttctcag gctcctgtga gcctcagtcc | 2243 |
| tgagaccaga gtcaagagga agtacacatc ccaatcaccc gtgtcaggat tcactctcag | 2303 |
| gagctgggtg gcaggagagg caatagcccc tgtggcaatt gcaggaccag ctggagcagg | 2363 |
| gttgcggtgt ctccgcggtg ctctcgccct gcccatggcc accccagact ctgatctcca | 2423 |
| ggaaccccat agcccctctc cacctcaccc catgttgatg cccagggtca ctcttgctac | 2483 |
| ccgctgggcc cccaaacccc cgctgcctct cttccttccc cccatccccc acctggtttt | 2543 |
| gactaatcct gcttccctct ctgggcctgg ctgccgggat ctgggtccc taagtccctc | 2603 |
| tcttttaaaga acttctgcgg gtcagactct gaagccgagt tgctgtgggc gtgcccggaa | 2663 |
| gcagagcgcc acactcgctg cttaagctcc cccagctctt tccagaaaac attaaactca | 2723 |
| gaattgtgtt ttcagcaaaa aaaaaaaaaa aaaaagggc ggccgc | 2769 |

<210> SEQ ID NO 2
<211> LENGTH: 281
<212> TYPE: PRT
<213> ORGANISM: Homo sapien

-continued

```
<400> SEQUENCE: 2

Met Gly Ser Arg Gly Gln Gly Leu Leu Ala Tyr Cys Leu Leu Leu
 1               5                  10                  15

Ala Phe Ala Ser Gly Leu Val Leu Ser Arg Val Pro His Val Gln Gly
             20                  25                  30

Glu Gln Gln Glu Trp Glu Gly Thr Glu Glu Leu Pro Ser Pro Pro Asp
         35                  40                  45

His Ala Glu Arg Ala Glu Gln His Glu Lys Tyr Arg Pro Ser Gln
 50                  55                  60

Asp Gln Gly Leu Pro Ala Ser Arg Cys Leu Arg Cys Cys Asp Pro Gly
 65                  70                  75                  80

Thr Ser Met Tyr Pro Ala Thr Ala Val Pro Gln Ile Asn Ile Thr Ile
                 85                  90                  95

Leu Lys Gly Glu Lys Gly Asp Arg Gly Asp Arg Gly Leu Gln Gly Lys
                100                 105                 110

Tyr Gly Lys Thr Gly Ser Ala Gly Ala Arg Gly His Thr Gly Pro Lys
            115                 120                 125

Gly Gln Lys Gly Ser Met Gly Ala Pro Gly Glu Arg Cys Lys Ser His
        130                 135                 140

Tyr Ala Ala Phe Ser Val Gly Arg Lys Lys Pro Met His Ser Asn His
145                 150                 155                 160

Tyr Tyr Gln Thr Val Ile Phe Asp Thr Glu Phe Val Asn Leu Tyr Asp
                165                 170                 175

His Phe Asn Met Phe Thr Gly Lys Phe Tyr Cys Tyr Val Pro Gly Leu
            180                 185                 190

Tyr Phe Phe Ser Leu Asn Val His Thr Trp Asn Gln Lys Glu Thr Tyr
        195                 200                 205

Leu His Ile Met Lys Asn Glu Glu Val Val Ile Leu Phe Ala Gln
    210                 215                 220

Val Gly Asp Arg Ser Ile Met Gln Ser Gln Ser Leu Met Leu Glu Leu
225                 230                 235                 240

Arg Glu Gln Asp Gln Val Trp Val Arg Leu Tyr Lys Gly Glu Arg Glu
                245                 250                 255

Asn Ala Ile Phe Ser Glu Glu Leu Asp Thr Tyr Ile Thr Phe Ser Gly
            260                 265                 270

Tyr Leu Val Lys His Ala Thr Glu Pro
        275                 280

<210> SEQ ID NO 3
<211> LENGTH: 247
<212> TYPE: PRT
<213> ORGANISM: Homo sapien

<400> SEQUENCE: 3

Met Leu Leu Leu Gln Ala Leu Leu Phe Leu Leu Ile Leu Pro Ser His
 1               5                  10                  15

Ala Glu Asp Asp Val Thr Thr Thr Glu Glu Leu Ala Pro Ala Leu Val
             20                  25                  30

Pro Pro Pro Lys Gly Thr Cys Ala Gly Trp Met Ala Gly Ile Pro Gly
         35                  40                  45

His Pro Gly His Asn Gly Thr Pro Gly Arg Asp Gly Arg Asp Gly Thr
     50                  55                  60

Pro Gly Glu Lys Gly Glu Lys Gly Asp Ala Gly Leu Leu Gly Pro Lys
 65                  70                  75                  80
```

```
Gly Glu Thr Gly Asp Val Gly Met Thr Gly Ala Glu Gly Pro Arg Gly
                85                  90                  95

Phe Pro Gln Thr Pro Gly Arg Lys Gly Glu Pro Gly Glu Ala Ala Tyr
                100                 105                 110

Met Tyr Arg Ser Ala Phe Ser Val Gly Leu Glu Thr Arg Val Thr Val
                115                 120                 125

Pro Asn Val Pro Ile Arg Phe Thr Lys Ile Phe Tyr Asn Gln Gln Asn
                130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
                180                 185                 190

Gln Glu Lys Asn Val Asp Gln Ala Ser Gly Ser Val Leu Leu His Leu
                195                 200                 205

Glu Val Gly Asp Gln Val Trp Leu Gln Val Tyr Gly Asp Gly Asp His
                210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide ZC12447

<400> SEQUENCE: 4
atggggcacg cgactcagga ccaggccaga                                      30

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide ZC695

<400> SEQUENCE: 5
gatttaggtg acactatag                                                  19

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide ZC694

<400> SEQUENCE: 6
taatacgact cactataggg                                                 20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide ZC13210

<400> SEQUENCE: 7
```
aagcaccggg aagcagggag                    20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide ZC13588

<400> SEQUENCE: 8
cgggcacgta gcagtagaac                    20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide ZC13532

<400> SEQUENCE: 9
gagagggctg aagaacaaca                    20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide ZC13641

<400> SEQUENCE: 10
aaggtggcga gaggaaagga                    20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide ZC13586

<400> SEQUENCE: 11
tgttcaccgg caagttctac                    20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide ZC13651

<400> SEQUENCE: 12
ctttgtcctc cacggtttac                    20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide ZC13622

<400> SEQUENCE: 13
tttcctctcg ccaccttcca                    20

<210> SEQ ID NO 14
<211> LENGTH: 21
<212> TYPE: DNA

```
<213> ORGANISM: Artificial Sequence
<220> FEATURE:
<223> OTHER INFORMATION: Oligonucleotide ZC13625

<400> SEQUENCE: 14
cttcggctgc ttctaaccaa c                                              21

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide ZC13650

<400> SEQUENCE: 15
gtaaaccgtg gaggacaaag                                                20

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide  ZC13859

<400> SEQUENCE: 16
gctgccaacc aacacaacca c                                              21

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide ZC13624

<400> SEQUENCE: 17
gcaggattag tcaaaacc                                                  18

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide ZC13531

<400> SEQUENCE: 18
aacatggggt gaggtggaga                                                20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide ZC13587

<400> SEQUENCE: 19
tcctcgtggg ctaagcatca                                                20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide ZC13623

<400> SEQUENCE: 20
atctccagga accccatagc                                                20
```

```
<210> SEQ ID NO 21
<211> LENGTH: 18
<212> TYPE: DNA
<213> ORGANISM: Artificial Sequence
<220> FEATURE:
<223> OTHER INFORMATION: Oligonucleotide ZC14444

<400> SEQUENCE: 21
tctccaggaa ccccatag                                              18

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide ZC14445

<400> SEQUENCE: 22
gcaggattag tcaaaacc                                              18

<210> SEQ ID NO 23
<211> LENGTH: 843
<212> TYPE: DNA
<213> ORGANISM: Artificial Sequence
<220> FEATURE:
<223> OTHER INFORMATION: Degenerate nucleotide sequence encoding zsig37
      polypeptide

<400> SEQUENCE: 23
atgggnwsnm gnggncargg nytnytnytn gcntaytgyy tnytnytngc nttygcnwsn    60
ggnytngtny tnwsnmgngt nccncaygtn carggngarc arcargartg ggarggnacn   120
gargarytnc cnwsnccncc ngaycaygcn garmgncng argarcarca ygaraartay   180
mgnccnwsnc argaycargg nytnccngcn wsnmgntgyy tnmgntgytg ygayccnggn   240
acnwsnatgt ayccngcnac ngcngtnccn carathaaya thacnathyt naarggngar   300
aarggngaym gnggngaymg nggnytncar ggnaartayg gnaaracngg nwsngcnggn   360
gcnmgnggnc ayacnggncc naarggncar aarggnwsna tgggngcncc nggngarmgn   420
tgyaarwsnc aytaygcngc nttywsngtn ggnmgnaara arccnatgca ywsnaaychay   480 taytaycara cngtnathtt ygayacngar ttygtnaayy tntaygayca yttyaayatg   540
ttyacnggna arttytaytg ytaygtnccn ggnytntayt tyttywsnyt naaygtncay   600
acntggaayc araargarac ntayytncay athatgaara aygargarga rgtngtnath   660
ytnttygcnc argtnggnga ymgnwsnath atgcarwsnc arwsnytnat gytngarytn   720
mgngarcarg aycargtntg ggtnmgnytn tayaarggng armgngaraa ygcnathtty   780
wsngargary tngayacnta yathacntty wsnggntayy tngtnaarca ygcnacngar   840 ccn                                                               843

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide ZC15040

<400> SEQUENCE: 24
actcattcta gactagggct cggt                                        24
```

```
<210> SEQ ID NO 25
<211> LENGTH: 24
<212> TYPE: DNA
<213> ORGANISM: Artificial Sequence
<220> FEATURE:
<223> OTHER INFORMATION: Oligonucleotide ZC15033

<400> SEQUENCE: 25
atgaatggat ccctggtcct gagt                                              24

<210> SEQ ID NO 26
<211> LENGTH: 7
<212> TYPE: PRT
<213> ORGANISM: Artificial Sequence
<220> FEATURE:
<223> OTHER INFORMATION: Glu-Glu affinity tag peptide

<400> SEQUENCE: 26

Glu Glu Tyr Met Pro Met Glu
 1               5

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide ZC15721

<400> SEQUENCE: 27
ctgtaggaat tcatgggctc ccgt                                              24

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide ZC15035

<400> SEQUENCE: 28
attcatggat ccgggctcgg tggc                                              24

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide ZC13006

<400> SEQUENCE: 29
ggctgtcctc taagcgtcac                                                   20

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide ZC13007

<400> SEQUENCE: 30
aggggtcaca gggatgcca                                                    19

<210> SEQ ID NO 31
<211> LENGTH: 6
<212> TYPE: PRT
<213> ORGANISM: Artificial Sequence
<220> FEATURE:
<223> OTHER INFORMATION: Glu-Glu peptide
```

-continued

```
<400> SEQUENCE: 31

Gly Tyr Met Pro Val Asp
 1               5

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide ZC6768

<400> SEQUENCE: 32
gcaattaacc ctcactaaag ggaac                                          25

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide ZC18297

<400> SEQUENCE: 33
tcctgaaagg cgagaaaggt g                                              21

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide ZC18298

<400> SEQUENCE: 34
ttccctgagt ctgagctagg                                                20

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide ZC18402

<400> SEQUENCE: 35
tccagagtga ctggggaagt g                                              21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide ZC18403

<400> SEQUENCE: 36
agtgacgagt tcgacaccta c                                              21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide ZC18456

<400> SEQUENCE: 37
tgtgttccca ttcctggaca c                                              21
```

```
<210> SEQ ID NO 38
<211> LENGTH: 21
<212> TYPE: DNA
<213> ORGANISM: Artificial Sequence
<220> FEATURE:
<223> OTHER INFORMATION: Oligonucleotide ZC18457

<400> SEQUENCE: 38
tccttccagc tggctggaaa g                                         21

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide ZC18560

<400> SEQUENCE: 39
agaatgcagg gataggtcag                                           20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide ZC18561

<400> SEQUENCE: 40
tcagaggatc ctgacagcag                                           20

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide ZC18687

<400> SEQUENCE: 41
tggacacgtg agagggactt c                                         21

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide ZC18688

<400> SEQUENCE: 42
agcagtagaa cttcccagtg                                           20

<210> SEQ ID NO 43
<211> LENGTH: 2559
<212> TYPE: DNA
<213> ORGANISM: Mus musculus
<220> FEATURE:
<221> NAME/KEY: CDS
<222> LOCATION: (70)...(912)
<223> OTHER INFORMATION: mouse ortholog

<400> SEQUENCE: 43
gaattcggat cctggaagag atgggattgt tataggcgga aagagagaaa cccagagaag    60 tccaggaag atg ggc tcc tgt gca cag gga ttc atg ctg gga tgc tgc ctg   111
         Met Gly Ser Cys Ala Gln Gly Phe Met Leu Gly Cys Cys Leu
           1               5                  10 ctg ctg gcc atc acc tgg ggc ccc atc ctg agc ctt gtg cca cgc gtt    159
Leu Leu Ala Ile Thr Trp Gly Pro Ile Leu Ser Leu Val Pro Arg Val
```

```
              15                  20                  25                  30
cag gag gaa caa cag gag tgg gaa gag aca gag gag ctg cca tct cct           207
Gln Glu Glu Gln Gln Glu Trp Glu Glu Thr Glu Glu Leu Pro Ser Pro
                    35                  40                  45 ctg gat cct gtg aca agg cct gaa gaa aca cga gag aag tat agc cct           255
Leu Asp Pro Val Thr Arg Pro Glu Glu Thr Arg Glu Lys Tyr Ser Pro
            50                  55                  60 cgc cag ggt gag gac ctc ccc act tct cgg tgc tac cga tgc tgt gac           303
Arg Gln Gly Glu Asp Leu Pro Thr Ser Arg Cys Tyr Arg Cys Cys Asp
        65                  70                  75 ccc agc aca cct gta tac cag aca att cct cca ccc cag atc aac atc           351
Pro Ser Thr Pro Val Tyr Gln Thr Ile Pro Pro Pro Gln Ile Asn Ile
    80                  85                  90 acc atc ctg aaa ggc gag aaa ggt gac cga ggg gat cga ggc ctc cag           399
Thr Ile Leu Lys Gly Glu Lys Gly Asp Arg Gly Asp Arg Gly Leu Gln
95                  100                 105                 110 ggg aag tac ggc aaa ata ggt tct aca ggt ccc agg ggc cat gtt ggc           447
Gly Lys Tyr Gly Lys Ile Gly Ser Thr Gly Pro Arg Gly His Val Gly
                115                 120                 125 ccc aaa ggg cag aag gga tcc att gga gcc cct ggg aac cac tgc aag           495
Pro Lys Gly Gln Lys Gly Ser Ile Gly Ala Pro Gly Asn His Cys Lys
            130                 135                 140 agc cag tac gca gcc ttc tcc gtg ggc cgg aag aag gct ttg cac agc           543
Ser Gln Tyr Ala Ala Phe Ser Val Gly Arg Lys Lys Ala Leu His Ser
        145                 150                 155 aac gac tac ttc cag ccc gtg gtc ttc gac acg gag ttt gtg aac ctc           591
Asn Asp Tyr Phe Gln Pro Val Val Phe Asp Thr Glu Phe Val Asn Leu
    160                 165                 170 tac aaa cac ttc aat atg ttc act ggg aag ttc tac tgc tat gtg ccg           639
Tyr Lys His Phe Asn Met Phe Thr Gly Lys Phe Tyr Cys Tyr Val Pro
175                 180                 185                 190 ggc atc tac ttc ttc agc ctc aac gtg cac act tgg aac cag aag gag           687
Gly Ile Tyr Phe Phe Ser Leu Asn Val His Thr Trp Asn Gln Lys Glu
                195                 200                 205 acg tac ctg cac atc atg aag aac gag gag gag gtg gtg atc ctg tat           735
Thr Tyr Leu His Ile Met Lys Asn Glu Glu Glu Val Val Ile Leu Tyr
            210                 215                 220 gcg cag gtg agc gac cgc agc atc atg cag agt cag agc ctg atg atg           783
Ala Gln Val Ser Asp Arg Ser Ile Met Gln Ser Gln Ser Leu Met Met
        225                 230                 235 gag ctg cgg gag gag gat gag gtc tgg gtg cgt ctc ttc aag ggc gag           831
Glu Leu Arg Glu Glu Asp Glu Val Trp Val Arg Leu Phe Lys Gly Glu
    240                 245                 250 cgt gag aac gcc att ttc agt gac gag ttc gac acc tac atc acc ttc           879
Arg Glu Asn Ala Ile Phe Ser Asp Glu Phe Asp Thr Tyr Ile Thr Phe
255                 260                 265                 270 agt ggc tac ctg gtc aag cca gcc tct gag ccc tagtggacac tcctgtggag         932
Ser Gly Tyr Leu Val Lys Pro Ala Ser Glu Pro
                275                 280 cttttgtgga ctgctgacct ccttgcctgg caccctgacc tatccctgca ttctacagac         992
actggagtcc tgccccgggc tgaccccatt ttctctctgc tccatcctgg cttccttggc        1052
cttggcttcc aaagttttgg cttttgacaa gatgcccttg ccactgggaa tcccaaagg         1112 atggtgcgat cccagatctg gctgctactc taagcagaga gctgccggca gatgaaatca       1172
ttgggcgggg agcctgtgag gatattgggg ggcctccagc tccttctgtg tacacagcct       1232
tagacgaccc tgtgctgtgt tgtcccgtgg ccacagggtg ttccagagca cagcccctgt       1292
gtgttcccat tcctggacac aagtaagcaa atatcatggg tttcttagga acgaagtcaa       1352
```

```
gcagaaaaga gaaagaaagg tggtgttagt tttggctttc cagccagctg gaaggaggga    1412
tggggagaga gagagagaga gagctatttg tattggggaa actgaggcat aggaaaaaca    1472
tgaatggcaa cagagtagct gcagtttgtg ggtttggaaa ccacatctga cttaactcta    1532
gatcacatat gagctttcct ggggacagca ggactgacct ccgagctctg ttgacatgct    1592
atagccttgc ccaggggctg gtcaatcttt ctgagccaca ctagtaaaag ggttggagga    1652
gaacagcaag tgcccctgt ggttggctct gggctggtgg cagcatcctg cttgccccaa     1712
ctcacaggat cctgacagca gctgggaacc tcagggactc ctgcagcttt ctctgtaaga    1772
aataaagctc ctactatgtc ccagtacctc tctgctctgc tccacttccc cagtcactct    1832 ggacccagg gtgggagggc tctcttgcct gttgggacat cagttcccct tcctccttct     1892
tggtgaatta accatggaag gaccagggct cggatttggg ttcccaaact gcccttcacc    1952
atccctagtg tcctgcttcc ttcccagttc agcatcctgt ctgggaactt gatactttaa    2012
cctgctagag cggatgagtc tgatagacct gcccagccct gacacagccc tagtcagctt    2072
atggacacgt gagagggact tcctttgaga cccagagctg gggtagagct ataaaaatct    2132
acctattccc gggtcaaccc caagtggtag aagaggacac aggctatccc gccctagctc    2192
agactcaggg aaggcctcag gcctgattgt ctgactgcag agagcctgtg ttctttcccc    2252
atctcacccc gtgttgatcc ccagggcctg ggccactgga tatctgcttt gtgccaacta    2312
ggccttgctt gctgcttcct ggtggcccctt ggttaggatc cctctctttt ccttctggag   2372
ctcaatgtac gtatatgcca cctccgaagg ggcttctgct ggtcagactc tccaagccac    2432
ttccatgggt gtgcctacag cagaggctgc tgcctcctgt gctctaccct gctctttcca    2492
gaaaacatta aacttgccat ggcgattcac agcaaaaaaa aaaaaaaaaa aaaaaaaagg    2552
gcggccg                                                              2559
```

<210> SEQ ID NO 44
<211> LENGTH: 281
<212> TYPE: PRT
<213> ORGANISM: Mus musculus

<400> SEQUENCE: 44

```
Met Gly Ser Cys Ala Gln Gly Phe Met Leu Gly Cys Cys Leu Leu Leu
 1               5                  10                  15

Ala Ile Thr Trp Gly Pro Ile Leu Ser Leu Val Pro Arg Val Gln Glu
            20                  25                  30

Glu Gln Gln Glu Trp Glu Glu Thr Glu Glu Leu Pro Ser Pro Leu Asp
        35                  40                  45

Pro Val Thr Arg Pro Glu Glu Thr Arg Glu Lys Tyr Ser Pro Arg Gln
    50                  55                  60

Gly Glu Asp Leu Pro Thr Ser Arg Cys Tyr Arg Cys Cys Asp Pro Ser
65                  70                  75                  80

Thr Pro Val Tyr Gln Thr Ile Pro Pro Gln Ile Asn Ile Thr Ile
                85                  90                  95

Leu Lys Gly Glu Lys Gly Asp Arg Gly Asp Arg Gly Leu Gln Gly Lys
            100                 105                 110

Tyr Gly Lys Ile Gly Ser Thr Gly Pro Arg Gly His Val Gly Pro Lys
        115                 120                 125

Gly Gln Lys Gly Ser Ile Gly Ala Pro Gly Asn His Cys Lys Ser Gln
    130                 135                 140

Tyr Ala Ala Phe Ser Val Gly Arg Lys Lys Ala Leu His Ser Asn Asp
```

-continued

```
        145                 150                 155                 160
Tyr Phe Gln Pro Val Val Phe Asp Thr Glu Phe Val Asn Leu Tyr Lys
            165                 170                 175

His Phe Asn Met Phe Thr Gly Lys Phe Tyr Cys Tyr Val Pro Gly Ile
            180                 185                 190

Tyr Phe Phe Ser Leu Asn Val His Thr Trp Asn Gln Lys Glu Thr Tyr
            195                 200                 205

Leu His Ile Met Lys Asn Glu Glu Val Val Ile Leu Tyr Ala Gln
            210                 215                 220

Val Ser Asp Arg Ser Ile Met Gln Ser Gln Ser Leu Met Met Glu Leu
225                 230                 235                 240

Arg Glu Glu Asp Glu Val Trp Val Arg Leu Phe Lys Gly Glu Arg Glu
            245                 250                 255

Asn Ala Ile Phe Ser Asp Glu Phe Asp Thr Tyr Ile Thr Phe Ser Gly
            260                 265                 270

Tyr Leu Val Lys Pro Ala Ser Glu Pro
            275                 280
```

ADIPOCYTE-SPECIFIC PROTEIN HOMOLOGS

REFERENCE TO RELATED APPLICATIONS

This application is a continuation of U.S. patent application Ser. No. 09/506,852, filed Feb. 17, 2000, now U.S. Pat. No. 6,566,499, which is a continuation-in-part of U.S. patent application Ser. No. 09/118,408, filed Jul. 17, 1998, now U.S. Pat. No. 6,265,544, which claims the benefit of U.S. patent application Ser. No. 60/053,154, filed Jul. 18, 1997, abandoned, all of which are herein incorporated by reference.

BACKGROUND OF THE INVENTION

Energy balance (involving energy metabolism, nutritional state, lipid storage and the like) is an important criteria for health. This energy homeostasis involves food intake and metabolism of carbohydrates and lipids to generate energy necessary for voluntary and involuntary functions. Metabolism of proteins can lead to energy generation, but preferably leads to muscle formation or repair. Among other consequences, a lack of energy homeostasis lead to over or under formation of adipose tissue.

Formation and storage of fat is insulin-modulated. For example, insulin stimulates the transport of glucose into cells, where it is metabolized into α-glycerophosphate which is used in the esterification of fatty acids to permit storage thereof as triglycerides. In addition, adipocytes (fat cells) express a specific transport protein that enhances the transfer of free fatty acids into adipocytes.

Adipocytes also secrete several proteins believed to modulate homeostatic control of glucose and lipid metabolism. These additional adipocyte-secreted proteins include adipsin, complement factors C3 and B, tumor necrosis factor α, the ob gene product and Acrp30. Evidence also exists suggesting the existence of an insulin-regulated secretory pathway in adipocytes. Scherer et al., *J. Biol. Chem.* 270 (45): 26746–9, 1995. Over or under secretion of these moieties, impacted in part by over or under formation of adipose tissue, can lead to pathological conditions associated directly or indirectly with obesity or anorexia.

Acrp30 is a 247 amino acid polypeptide that is expressed exclusively by adipocytes. The Acrp30 polypeptide is composed of a amino-terminal signal sequence, a 27 amino acid stretch of no known homology, 22 perfect Gly-Xaa-Pro or imperfect Gly-Xaa-Xaa collagen repeats and a carboxy terminal globular domain. See, Scherer et al. as described above and International Patent Application No. WO96/39429. Acrp3O, an abundant human serum protein regulated by insulin, shares structural similarity, particularly in the carboxy-terminal globular domain, to complement factor C1q and to a summer serum protein of hibernating Siberian chipmunks (Hib27). Expression of Acrp30 is induced over 100-fold during adipocyte differentiation. Acrp30 is suggested for use in modulating energy balance and in identifying adipocytes in test samples.

Another secreted protein that appears to be exclusively produced in adipocytes is apM1, described, for example, in Maeda et al., *Biochem. Biophys. Res. Comm.* 221:286–9, 1996. A 4517 bp clone had a 244 amino acid open reading frame and a long 3' untranslated region. The protein included a signal sequence, an amino-terminal non-collagenous sequence, 22 collagen repeats (Gly-XAA-Pro or Gly-Xaa-Xaa), and a carboxy-terminal region with homology to collagen X, collagen VIII and complement protein C1q.

Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is therefore composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain.

Molecules capable of modulating energy homeostasis are sought for the study of this phenomena and for the prevention or treatment of imbalances. Also, molecules capable of modulating adipocyte secretory pathways are also sought as indirect energy homeostasis modulators and as research reagents.

The present invention provides such polypeptides for these and other uses that should be apparent to those skilled in the art from the teachings herein.

SUMMARY OF THE INVENTION

Within one aspect the invention provides an isolated polypeptide comprising a sequence of amino acid residues that is at least 75% identical in amino acid sequence to residues 26–281 of SEQ ID NO:2, wherein the sequence comprises: Gly-Xaa-Xaa or Gly-Xaa-Pro repeats forming a collagen domain, wherein Xaa is any amino acid; and a carboxy-terminal globular portion. Within one embodiment the polypeptide comprises a sequence of amino acid residues that is at least 90% identical in amino acid sequence to residues 22–281 of SEQ ID NO:2. Within another embodiment the polypeptide comprises an amino acid sequence that is at least 90% identical in amino acid sequence to residues 26–281 of SEQ ID NO:2. Within in a related embodiment any differences between the polypeptide and SEQ ID NO:2 are due to conservative amino acid substitutions. Within yet another embodiment the collagen domain consists of 13 Gly-Xaa-Xaa repeats and 1 Gly-Xaa-Pro repeat. Within another embodiment the globular domain consists of ten beta sheets. Within a related embodiment the beta sheets are associated with amino acid residues correspondging to 147–151, 170–172, 178–181, 191–203, 207–214, 219–225, 227–239, 244–250, and 269–274 of SEQ ID NO:2. Within another embodiment the polypeptide comprises residues 1–281 of SEQ ID NO:2 or residues 1–281 of SEQ ID NO:44. Within yet another embodiment the polypeptide is complexed to a second polypeptide to form a oligomer. Within a related ebodiment the polypeptides are complexed by intermolecular disulfide bonds. Within another embodiment the oligomer is a trimer. Within another embodiment the oligomer is a hexamer. Within still another embodiment the multimer is an 18mer. Within a related embodiment linked amino terminally or carboxy terminally to a moiety selected from the group consisting of affinity tags, toxins, radionucleotides, enzymes and fluorophores. Within another embodiment the polypeptide further comprises comprising a proteolytic cleavage site between the sequence of amino acid residues and the affinity tag.

The invention also provides an isolated polypeptide selected from the group consisting of: a) a polypeptide having a sequence of amino acid residues that is 75% identical in amino acid sequence to amino acid residue 99 to amino acid residue 140 of SEQ ID NO:2; b) a polypeptide having a sequence of amino acid residues that is 75% identical in amino acid sequence to amino acid residue 140 or 141 to amino acid residue 281 of SEQ ID NO:2; and c) a polypeptide having a sequence of amino acid residues that is 75% identical in amino acid sequence to amino acid residue 99 to 281 of SEQ ID NO:2.

The invention also provides fusion protein consisting essentially of a first portion and a second portion joined by a peptide bond, the first portion comprising a polypeptide selected from the group consisting of: a) a polypeptide comprising a sequence of amino acid residues that is at least 75% identical in amino acid sequence to amino acid residue 26 to amino acid residue 281 of SEQ ID NO:2; b) a polypeptide comprising a sequence of amino acid residues as shown in SEQ ID NO:2 from amino acid residue 1, 22 or 26 to amino acid residue 281; c) a polypeptide comprising a sequence of amino acid residues as shown in SEQ ID NO:44 from amino acid residue 1, 22 or 26 to amino acid residue 281; d) a portion of the zsig37 polypeptide as shown in SEQ ID NO:2 or SEQ ID NO:44, containing the collagen-like domain or a portion of the collagen-like domain capable of dimerization or oligomerization; e) a portion of the zsig37 polypeptide as shown in SEQ ID NO:2 or SEQ ID NO:44 containing the globular-like domain or an active portion of the globular-like domain; or f) a portion of the zsig37 polypeptide as shown in SEQ ID NO:2 or SEQ ID NO:44 including the collagen-like domain and the globular domain; and the second portion comprising another polypeptide. In a one embodiment the first portion is selected from the group consisting of: a) a polypeptide having the sequence of amino acid residue 99 to amino acid residue 140 of SEQ ID NO:2 or SEQ ID NO:44; b) a polypeptide having the sequence of amino acid residue 140 or 141 to amino acid residue 281 of SEQ ID NO:2 or SEQ ID NO:44; c) a polypeptide having the sequence of amino acid residue 99 to 281 of SEQ ID NO:2 or SEQ ID NO:44.

The invention also provides a fusion protein comprising a secretory signal sequence having the amino acid sequence of amino acid residues 1–21 or 1–25 of SEQ ID NO:2 or SEQ ID NO:44, wherein the secretory signal sequence is operably linked to an additional polypeptide.

Within another aspect the invention provides an expression vector comprising the following operably linked elements: a transcription promoter; DNA sequence encoding a polypeptide as described above; and a transcription terminator. Within one embodiment the secretory signal sequence comprises residues 1–21 or 1–25 of SEQ ID NO:2 or SEQ ID NO:44.

The invention also provides a cultured cell into which has been introduced an expression vector comprising the following operably linked elements: a transcription promoter; a DNA segment encoding a polypeptide as described above; and a transcription terminator, wherein the cell expresses the polypeptide encoded by the DNA segment.

The invention also provides a method of producing a polypeptide comprising: culturing a cell into which has been introduced an expression vector comprising the following operably linked elements: a transcription promoter; a DNA segment encoding a polypeptide as described above; and a transcription terminator; whereby the cell expresses the polypeptide encoded by the DNA segment; and recovering the expressed polypeptide.

The invention further provides a polypeptide as described above; in combination with a pharmaceutically acceptable vehicle.

Within another aspect the invention also provides an antibody that specifically binds to an epitope of a polypeptide as described above. Also provided is a binding protein that specifically binds to an epitope of a polypeptide as described above.

Within another aspect is provided an isolated polynucleotide encoding a polypeptide as described above. Within one embodiment the polynucleotide is DNA.

Also provided is an isolated polynucleotide selected from the group consisting of, a) a sequence of nucleotides from nucleotide 465 to nucleotide 688 of SEQ ID NO:1; b) a sequence of nucleotides from nucleotide 688 to nucleotide 1016 of SEQ ID NO:1; c) a equence of nucleotides from nucleotide 691 to nucleotide 1016 of SEQ ID NO:1; d) a sequence of nucleotides from nucleotide 465 to nucleotide 1016 of SEQ ID NO:1; e) a sequence of nucleotides from nucleotide 364to nucleotide 490 of SEQ ID NO:43; f) a sequence of nucleotides from nucleotide 490 to nucleotide 912 of SEQ ID NO:43; g) a sequence of nucleotides from nucleotide 364 to nucleotide 912 of SEQ ID NO:43; h) a sequence of nucleotides from nucleotide 364 to nucleotide 490 of SEQ ID NO:43; i) a polynucleotide encoding a polypeptide having a sequence of amino acid residues that is at least 75% identical in amino acid sequence to amino acid residue 99, 140 or 141 to amino acid residue 281 of SEQ ID NO:2; j) a polynucleotide encoding a polypeptide having a sequence of amino acid residues that is at least 75% identical in amino acid sequence to amino acid residue 99 to amino acid residue 140 of SEQ ID NO:2; k) nucleotide sequences complementary to a), b), c), d), e), f), g), h), i) or j) and 1) degenerate nucleotide sequences of a), b), c), d), e), f), g), h), i), j) or k).

The invention also provides an isolated polynucleotide encoding a fusion protein consisting essentially of a first portion and a second portion joined by a peptide bond, the first portion is selected from the group consisting of: a) a polypeptide comprising a sequence of amino acid residues that is at least 75% identical in amino acid sequence to amino acid residue 26 to amino acid residue 281 of SEQ ID NO:2; b) a polypeptide comprising a sequence of amino acid residues as shown in SEQ ID NO:2 from amino acid residue 1, 22 or 26 to amino acid residue 281; c) a polypeptide comprising a sequence of amino acid residues as shown in SEQ ID NO:44 from amino acid residue 1, 22 or 26 to amino acid residue 281; d) a portion of the zsig37 polypeptide as shown in SEQ ID NO:2 or SEQ ID NO:44, containing the collagen-like domain or a portion of the collagen-like domain capable of dimerization or oligomerization; e) a portion of the zsig37 polypeptide as shown in SEQ ID NO:2 or SEQ ID NO:44 containing the globular-like domain or an active portion of the globular-like domain; or f) a portion of the zsig37 polypeptide as shown in SEQ ID NO:2 or SEQ ID NO:44 including the collagen-like domain and the globular domain; and the second portion comprising another polypeptide.

Also provided is an isolated polynucleotide encoding a fusion protein comprising a secretory signal sequence having the amino acid sequence of amino acid residues 1–21 or 1–25 of SEQ ID NO:2, wherein the secretory signal sequence is operably linked to an additional polypeptide.

The invention provides an isolated polynucleotide comprising the sequence of nucleotide 1 to nucleotide 843 of SEQ ID NO:23.

The invention also provides an oligonucleotide probe or primer comprising at least 14 contiguous nucleotides of a polynucleotide of SEQ ID NO:23 or a sequence complementary to SEQ ID NO:23.

BRIEF DESCRIPTION OF THE DRAWINGS

FIG. 1 illustrates a multiple alignment of and zsig37 polypeptide of the present invention and HUMUPST2_1

(Maeda et al., *Biochem. Biophys. Res. Comm.* 221(2): 286–9, 1996); C1QA__HUMAN (Sellar et al., *Biochem. J.* 274: 481–90, 1991, Reid, *Biochem. J.* 179:367–71, 1979, and Reid et al., *Biochem. J.* 203:559–69, 1982); HP25__TAMAS (Takamatsu et al., *Mol. Cell. Biol.* 13:1516–21, 1993 and Kondo & Kondo, *J. Biol. Chem.* 267:473–8, 1992); HP27__TAMAS (Takamatsu et al. and Kondo & Kondo referenced above); and CERL__RAT (Wada & Ohtani, *Brain Res. Mol. Brain Res.* 9:71–7, 1991).

FIG. 2 is a matrix showing percent amino acid identity in a comparison of the six proteins shown in the multiple alignment FIG. 1.

DETAILED DESCRIPTION OF THE INVENTION

Prior to setting forth the invention in detail, it may be helpful to the understanding thereof to define the following terms.

The term "affinity tag" is used herein to denote a peptide segment that can be attached to a polypeptide to provide for purification or detection of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–1210, 1988; available from Eastman Kodak Co., New Haven, Conn.), streptavidin binding peptide, or other antigenic epitope or binding domain. See, in general Ford et al., *Protein Expression and Purification* 2:95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as diners or alternatively glycosylated or derivatized forms.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides". "Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having homology to an adipocyte complement related protein (Acrp30). See, for example, Scherer et al., *J. Biol. Chem.* 270(45): 26746–9, 1995. The polypeptide Acrp30 is shown in SEQ ID NO:3. Acrp30 appears to be highly related to human apM1 (HUMUPST2_1 in FIGS. 1 and 2), with the most significant differences observed in the secretory sequence.

The novel DNA sequence encodes a polypeptide having an amino-terminal signal sequence, an adjacent N-terminal region of non-homology, a truncated collagen domain composed of Gly-Xaa-Xaa or Gly-Xaa-Pro repeats and a carboxy-terminal globular portion. The novel polynucleotide sequence also contains a long 3' untranslated region. The general polypeptide structure set forth above is shared by Acrp30 and HUMUPST2_1, except that the collagen-like domain of each of those proteins is longer than that of zsig37 polypeptides. Also, the HUMUPST2_1 DNA sequence is characterized by a long 3' untranslated region. Moreover, Acrp30 and all of the sequences aligned in FIG.

1, with the exception of CERL_RAT, share a conserved cysteine residue at position 187 of zsig37 polypeptide as shown in FIG. 1 and SEQ ID NO:2. Other regions of homology, found in the carboxy-terminal globular portion in the aligned proteins, are identified herein as useful primers for searching for other family members. Acrp3O, for example, would be identified in a search using the primers. Also, the zsig37 polypeptides of the present invention include a putative N-linked glycosylation site at amino acid 93 (Asn) of SEQ ID NO:2.

Analysis of the tissue distribution of the mRNA corresponding to this novel DNA using a 30 base probe (SEQ ID NO:4) showed that expression was highest in heart and placenta, with relatively less intense signals in kidney, ovary, adrenal gland and skeletal muscle and lower signals in a wide variety of other tissues present on the Northern blot. The polypeptide has been designated zsig37 polypeptide.

The novel zsig37 polypeptides of the present invention were initially identified by querying an EST database for secretory signal sequences, characterized by an upstream methionine start site, a hydrophobic region of approximately 13 amino acids and a cleavage site, in an effort to select for secreted proteins. Polypeptides corresponding to ESTs meeting those search criteria were compared to known sequences to identify secreted proteins having homology to known ligands. A single EST sequence was discovered and predicted to be a secreted protein. The novel polypeptide encoded by the full length cDNA enable the identification of a homolog relationship with adipocyte complement related protein Acrp30 (SEQ ID NO:3) and adipocyte secreted protein apM1 (HUMUPST2_1 in FIGS. 1 and 2). Somewhat more distant homology was also identified to complement component C1Q A chain, two factors observed in the active state of hibernating Siberian woodchucks (HP25_TAMAS and HP27_TAMAS) and a rat brain protein (CERL_RAT), as shown in FIGS. 1 and 2.

The full sequence of the zsig37 polypeptide was obtained from a single clone believed to contain it, wherein the clone was-obtained from a brain tumor tissue library. Other libraries that might also be searched for such clones include heart, placenta, kidney, ovary, adrenal gland, skeletal muscle, adipose tissue and the like.

The nucleotide sequence of the N-terminal EST is described in SEQ ID NO:1, and its deduced amino acid sequence is described in SEQ ID NO:2. As described generally above, the zsig37 polypeptide includes a signal sequence, ranging from amino acid 1 (Met) to amino acid residue 21 (Gly). An alternative signal sequence ranges from amino acid 1 (Met) to amino acid 25 (Ser). The mature polypeptide therefore ranges from amino acid 22 (Leu) or 26 (Arg) to amino acid 281 (Pro). Within the mature polypeptide, an N-terminal region of no known homology is found, ranging between amino acid residue 22 (Leu) and 98 (Lys). In addition, a truncated collagen domain is found between amino acid 99 (Gly) and 140 (Arg). In the truncated collagen domain, 1 perfect Gly-Xaa-Pro and 13 imperfect Gly-Xaa-Xaa repeats are observed. In contrast, Acrp30 contains 22 perfect or imperfect repeats. The zsig37 polypeptide also includes a carboxy-terminal globular domain, ranging from about amino acid 141 (Cys) to 281 (Pro). Zsig37 polypeptide, HUMUPST2_1 and Acrp30 appear to be homologous within the collagen domain and in the globular domain, but not in the N-terminal portion of the mature polypeptide.

Another aspect of the present invention includes zsig37 polypeptide fragments. Preferred fragments include the collagen-like domain of zsig37 polypeptides, ranging from amino acid 99 (Gly) to amino acid 140 (Arg) of SEQ ID NO:2, a portion of the zsig37 polypeptide containing the collagen-like domain or a portion of the collagen-like domain capable of dimerization or oligomerization. These fragments are particularly useful in the study of collagen dimerization or oligomerization or in formation of fusion proteins as described more fully below. Polynucleotides encoding such fragments are also encompassed by the present invention, including the group consisting of (a) polynucleotide molecules comprising a sequence of nucleotides as shown in SEQ ID NO:1 from nucleotide 1, 171, 234, 246 or 465 to nucleotide 589; (b) polynucleotide molecules that encode a zsig37 polypeptide fragment that is at least 80% identical to the amino acid sequence of SEQ ID NO:2 from amino acid residue 99 (Gly) to amino acid residue 140 (Arg); (c) molecules complementary to (a) or (b); and (d) degenerate nucleotide sequences encoding a zsig37 polypeptide collagen-like domain fragment.

Other preferred fragments include the globular domain of zsig37 polypeptides, ranging from amino acid 140 (Arg) or 141 (Cys) to 281 (Pro) of SEQ ID NO:2, a portion of the zsig37 polypeptide containing the globular-like domain or an active portion of the globular-like domain. These fragments are particularly useful in the study or modulation of energy balance or neurotransmission, particularly diet- or stress-related neurotransmission. Anti-microbial activity may also be present in such fragments. Polynucleotides encoding such fragments are also encompassed by the present invention, including the group consisting of (a) polynucleotide molecules comprising a sequence of nucleotides as shown in SEQ ID NO:1 from nucleotide 587 or 590 to nucleotide 1016; (b) polynucleotide molecules that encode a zsig37 polypeptide fragment that is at least 80% identical to the amino acid sequence of SEQ ID NO:2 from amino acid residue 141 (Cys) to amino acid residue 281 (Pro); (c) molecules complementary to (a) or (b); and (d) degenerate nucleotide sequences encoding a zsig37-polypeptide globular domain fragment.

The globular C1q domain of ACRP30 has been determined to have a 10 beta strand "jelly roll" topology (Shapiro and Scherer, Curr. Biol. 8:335–8, 1998) that shows significant structural homology to the TNF family and the zsig37 sequence as represented by SEQ ID NO:2 contains all 10 beta-strands of this structure (amino acid residues 147–151, 170–172, 178–181, 185–188, 191–203, 207–214, 219–225, 227–238, 244–250, and 269–274 of SEQ ID NO:2). These strands have been designated "A", "A'", "B", "B'", "C", "D", "E", "F", "G" and "H" respectively.

Zsig37 has two receptor binding loops, at amino acid residues 152–180.and 21.3–226. Amino acid residues 191 (Gly), 193 (Tyr), 238 (Leu) and 272 (Gly) appear to be conserved across the superfamily including CD40, TNFα, TNFβ, ACRP30 and zsig37.

Another zsig37 polypeptide fragment of the present invention include both the collagen-like domain and the globular domain ranging from amino acid residue 99 (Gly) to 281 (Pro) of SEQ ID NO:2. Polynucleotides encoding such fragments are also encompassed by the present invention, including the group consisting of (a) polynucleotide molecules comprising a sequence of nucleotides as shown in SEQ ID NO:1 from nucleotide 465 to nucleotide 1016; (b) polynucleotide molecules that encode a zsig37 polypeptide fragment that is at least 80% identical to the amino acid sequence of SEQ ID NO:2 from amino acid residue 99 (Gly) to amino acid residue 281 (Pro); (c) molecules complementary to (a) or (b); and (f) degenerate nucleotide sequences encoding a zsig37 polypeptide collagen-like domain-globular domain fragment.

The present invention also contemplates degenerate probes based upon the polynucleotides described above. Probes corresponding to complements of the polynucleotides set forth above are also encompassed.

The present invention also provides polynucleotide molecules, including DNA and RNA molecules, that encode the zsig37 polypeptides disclosed herein. Those skilled in the art will readily recognize that, in view of the degeneracy of the genetic code, considerable sequence variation is possible among these polynucleotide molecules. SEQ ID NO:23 is a degenerate DNA sequence that encompasses all DNAs that encode the zsig37 polypeptide of SEQ ID NO:2. Those skilled in the art will recognize that the degenerate sequence of SEQ ID NO:23 also provides all RNA sequences encoding SEQ ID NO:2 by substituting U (uracil) for T (thymine). Thus, zsig37 polypeptide-encoding polynucleotides comprising nucleotide 1 to nucleotide 842 of SEQ ID NO:23 and their RNA equivalents are contemplated by the present invention. Table 1 sets forth the one-letter codes used within SEQ ID NO:23 to denote degenerate nucleotide positions. "Resolutions" are the nucleotides denoted by a code letter. "Complement" indicates the code for the complementary nucleotide(s). For example, the code Y denotes either C (cytosine) or T, and its complement R denotes A (adenine) or G (guanine), A being complementary to T, and G being complementary to C.

TABLE 1

| Nucleotide | Resolution | Complement | Resolution |
|---|---|---|---|
| A | A | T | T |
| C | C | G | G |
| C | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:23, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |

TABLE 2-continued

| Amino Acid | One Letter Code | Codons | Degenerate Codon |
|---|---|---|---|
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAO TAT | TAC |
| Trp | W | TGG | TGG |
| Ter | . | TAA TAG TGA | TRR |
| Asn\|Asp | B | RAY | |
| Glu\|Gln | Z | SAR | |
| Any | X | NNN | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et ail., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, Gene 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:23 serves as a template for optimizing expression of polynucleotides in various cell types and species commonly used in the art and disclosed herein. Sequences containing preferential codons can be tested and optimized for expression in various species, and tested for functionality as disclosed herein.

Zsig37 fragments may be evaluated with respect to their anti-microbial properties according to procedures known in the art. See, for example, Barsum et al., *Eur. Respir. J.* 8(5): 709–14, 1995; Sandovsky-Losica et al., *J. Med. Vet. Mycol* (*England*) 28(4): 279–87, 1990; Mehentee et al., *J. Gen. Microbiol* (*England*) 135 (Pt. 8): 2181–8, 198.9; Segal and Savage, *Journal of Medical and Veterinary Mycology*

24:477–479, 1986 and the like. If desired, zsig37 polypeptide fragment performance in this regard can be compared to proteins known to be functional in this regard, such as proline-rich proteins, lysozyme, histatins, lactoperoxidase or the like. In addition, zsig37 polypeptide fragments may be evaluated in combination with one or more anti-microbial agents to identify synergistic effects. One of ordinary skill in the art will recognize that the anti-microbial properties of zsig37 polypeptides, fusion proteins, agonists, antagonists and antibodies may be similarly evaluated.

As neurotransmitters or neurotransmission modulators, zsig37 polypeptide fragments as well as zsig37 polypeptides, fusion proteins, agonists, antagonists or antibodies of the present invention may also modulate calcium ion concentration, muscle contraction, hormone secretion, DNA synthesis or cell growth, inositol phosphate turnover, arachidonate release, phospholipase-C activation, gastric emptying, human neutrophil activation or ADCC capability, superoxide anion production and the like. Evaluation of these properties can be conducted by known methods, such as those set forth herein.

The impact of zsig37 polypeptide, fragment, fusion, agonist or antagonist on intracellular calcium level may be assessed by methods known in the art, such as those described by Dobrzanski et al., *Regulatory Peptides* 45:341–52, 1993, and the like. The impact of zsig37 polypeptide, fragment, fusion, agonist or antagonist on muscle contraction may be assessed by methods known in the art, such as those described by Smits & Lebebvre, *J. Auton. Pharmacol.* 14:383–92, 1994, Belloli et al., *J. Vet. Pharmacol. Therap.* 17:379–83, 1994, Maggi et al., *Regulatory Peptides* 53:259–74, 1994, and the like. The impact of zsig37 polypeptide, fragment, fusion, agonist or antagonist on hormone secretion may be assessed by methods known in the art, such as those for prolactin release described by Henriksen et al., *J. of Receptor & Signal Transduction Research* 15(1–4): 529–41, 1995, and the like. The impact of zsig37 polypeptide, fragment, fusion, agonist or antagonist on DNA synthesis or cell growth may be assessed by methods known in the art, such as those described by Dobrzanski et al., *Regulatory Peptides* 45:341–52, 1993, and the like. The impact of zsig37 polypeptide, fragment, fusion, agonist or antagonist on inositol phosphate turnover may be assessed by methods known in the art, such as those described by Dobrzanski et al., *Regulatory Peptides* 45:341–52, 1993, and the like.

Also, the impact of zsig37 polypeptide, fragment, fusion, agonist or antagonist on arachidonate release may be assessed by methods known in the art, such as those described by Dobrzanski et al., *Regulatory Peptides* 45:341–52, 1993, and the like. The impact of zsig37 polypeptide, fragment, fusion, agonist or antagonist on phospholipase-C activation may be assessed by methods known in the art, such as those described by Dobrzanski et al., *Regulatory Peptides* 45:341–52, 1993, and the like. The impact of zsig37 polypeptide, fragment, fusion, agonist or antagonist on gastric emptying may be assessed by methods known in the art, such as those described by Varga et al., *Eur. J. Pharmacol.* 286:109–112, 1995, and the like. The impact of zsig37 polypeptide, fragment, fusion, agonist or antagonist on human neutrophil activation and ADCC capability may be assessed by methods known in the art, such as those described by Wozniak et al., *Immunology* 78:629–34, 1993, and the like. The impact of zsig37 polypeptide, fragment, fusion, agonist or antagonist on superoxide anion production may be assessed by methods known in the art, such as those described by Wozniak et al., *Immunology* 78:629–34, 1993, and the like.

The present invention also provides zsig37 fusion proteins. For example, fusion proteins of the present invention encompass (1) a polypeptide selected from the group comprising: (a) polypeptide molecules comprising a sequence of amino acid residues as shown in SEQ ID NO:2 from amino acid residue 1 (Met), 22 (Leu) or 26 (Arg) to amino acid residue 281 (Pro); (b) polypeptide molecules ranging from amino acid 99 (Gly) to amino acid 140 (Arg) of SEQ ID NO:2, a portion of the zsig37 polypeptide containing the collagen-like domain or a portion of the collagen-like domain capable of dimerization or oligomerization; (c) polypeptide molecules ranging from amino acid 140 (Arg) or 141 (Cys) to 281 (Pro) of SEQ ID NO:2, a portion of the zsig37 polypeptide containing the globular-like domain or an active portion of the globular-like domain; or (d) polypeptide molecules ranging from amino acid 99 (Gly) to 281 (Pro), a portion of the zsig37 polypeptide including the collagen-like domain and the globular domain; and (2) another polypeptide. The other polypeptide may be alternative or additional globular domain, an alternative or additional collagen-like domain, a signal peptide to facilitate secretion of the fusion protein or the like. The globular domain of complement bind IgG, thus, the globular domain of zsig37 polypeptide, fragment or fusion may have a similar role.

Zsig37 polypeptides, ranging from amino acid 1 (Met) to amino acid 281 (Pro); the alternative mature zsig37 polypeptides, ranging from amino acid 22(Leu) or amino acid 26 (Arg) to amino acid 281 (Pro); or the alternative secretion leader fragments thereof, which fragments range from amino acid 1 (Met) to amino acid 21 (Gly) or amino acid 25 (Ser) may be used in the study of secretion of proteins from cells. In preferred embodiments of this aspect of the present invention, the mature polypeptides are formed as fusion proteins with putative secretory signal sequences; plasmids bearing regulatory regions capable of directing the expression of the fusion protein is introduced into test cells; and secretion of mature protein is monitored. In other preferred embodiments of this aspect of the present invention, the alternative secretion leader fragments are formed as fusion proteins with alternative proteins selected for secretion; plasmids bearing regulatory regions capable of directing the expression of the fusion protein are introduced into test cells; and secretion of the protein is monitored. The monitoring may be done by techniques known in the art, such as HPLC and the like.

The highly conserved amino acids, particularly those in the carboxy-terminal globular domain of zsig37 polypeptide, can be used as a tool to identify new family members. For instance, reverse transcription-polymerase chain reaction (RT-PCR) can be used to amplify sequences encoding the conserved motifs from RNA obtained from a variety of tissue sources. In particular, highly degenerate primers designed from conserved sequences are useful for this purpose. In particular, the following primers are useful for this purpose:

1) Amino acids 269–274 of SEQ ID NO:2 (corresponding to nucleotides 975–992 of SEQ ID NO:1);
2) Amino acids 191–196 of SEQ ID NO:2 (corresponding to nucleotides 741–758 of SEQ ID NO:1);
3) Amino acids 163–168 of SEQ ID NO:2 (corresponding to nucleotides 657–674 of SEQ ID NO:1);
4) Amino acids 173–178 of SEQ ID NO:2 (corresponding to nucleotides 687–704 of SEQ ID NO:1); and
5) Amino acids 243–248 of SEQ ID NO:2 (corresponding to nucleotides 897–914 of SEQ ID NO:1).

The present invention also contemplates degenerate probes based upon the polynucleotides described above. Probes corresponding to complements of the polynucleotides set forth above are also encompassed.

Within preferred embodiments of the invention the isolated polynucleotides will hybridize to similar sized regions of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration up to about 0.03 M at pH 7 and the temperature is at least about 60° C.

Within another aspect of the present invention there is provided a pharmaceutical composition comprising purified zsig37 polypeptide in combination with a pharmaceutically acceptable vehicle. This pharmaceutical composition will be used to modulate energy balance in mammals or to protect endothelial cells from injury.

With regard to modulating energy balance, zsig37 polypeptides modulate cellular metabolic reactions. Such metabolic reactions include adipogenesis, gluconeogenesis, glycogenolysis, lipogenesis, glucose uptake, protein synthesis, thermogenesis, oxygen utilization and the like. The expression pattern of zsig37 polypeptide indicates expression in endothelial cell tissues. With regard to endothelial cell protection, zsig37 polypeptide may be used in organ preservation, for cryopreservation, for surgical pretreatment to prevent injury due to ischemia and/or inflammation or in like procedures. Expression of zsig37 polypeptide in the heart suggests that the protein may modulate acetylcholine and/or norepinephrine release. Zsig37 polypeptides may also find use as neurotransmitters or as modulators of neurotransmission, as indicated by expression of the polypeptide in tissues associated with the sympathetic or parasympathetic nervous system. In this regard, zsig37 polypeptides may find utility in modulating nutrient uptake, as demonstrated, for example, by 2-deoxy-glucose uptake in the brain or the like.

Among other methods known in the art or described herein, mammalian energy balance may be evaluated by monitoring one or more of the following metabolic functions: adipogenesis, gluconeogenesis, glycogenolysis, lipogenesis, glucose uptake, protein synthesis, thermogenesis, oxygen utilization or the like. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogenolysis. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zsig37 polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation at the ob (obese) locus. Such ob/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except db/db, mice also display a diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^3$H or $^{14}$C-labeled deoxyglucose is added to ~50 1M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytocholasin b, an inhibitor of glucose transport. Other methods include those described by, for example, Manchester et al., *Am. J. Physiol.* 266 (*Endocrinol. Metab.* 29):E326–E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides*, W. Colmers and C. Wahlestedt (eds.), Humana Press, Ottawa, 1993, pp. 457–509; C. Billington et al., *Am. J. Physiol.* 260:R321, 1991; N. Zarjevski et al., *Endocrinoloqy* 133:1753, 1993; C. Billington et al., *Am. J. Physiol.* 266:R1765, 1994; Heller et al., *Am. J. Physiol.* 252(4 *Pt* 2): R661–7, 1987; and Heller et al., *Am. J. Physiol.* 245(3): R321–8, 1983. Also, metabolic rate, which may be measured by a variety of techniques, is an indirect measurement of thermogenesis.

Oxygen utilization may be evaluated as described by Heller et al., *Pflugers Arch* 369(1): 55–9, 1977. This method also involved an analysis of hypothalmic temperature and metabolic heat production. Oxygen utilization and thermoregulation have also been evaluated in humans as described by Haskell et al., *J. Appl. Physiol.* 51(4): 948–54, 1981.

Among other methods known in the art or described herein, mammalian endothelial cell tissue protection may be evaluated by monitoring the function of endothelial tissue. For example, the function of the heart (aorta) may be evaluated by monitoring acetylcholine release, norepinephrine release or like parameters. These parameters are monitored by techniques (assays or animal models) known to one of ordinary skill in the art, as is more fully set forth below.

Acetylcholine and norepinephrine release may be monitored by HPLC. Levy, *Electrophysiology of the Sinoatrial and Atrioventricular Nodes*, Alan R. Liss, Inc., 187–197, 1998, describe measurement of norepinephrine in coronary sinus effluent. In addition, animals may be electrically paced, with the results monitored as described by Elsner, *European Heart Journal* 16(Supplement N) 52–8, 1995, and Reiffel and Kuehnert, *PACE* 17 (Part 1):349–65, 1994.

Among other methods known in the art or described herein, neurotransmission functions may be evaluated by monitoring 2-deoxy-glucose uptake in the brain. This parameter is monitored by techniques (assays or animal models) known to one of ordinary skill in the art, for example, autoradiography. Useful monitoring techniques are described, for example, by Kilduff et al., *J. Neurosci.* 10 2463–75, 1990, with related techniques used to evaluate the "hibernating heart" as described in Gerber et al. *Circulation* 94(4): 651–8, 1996, and Fallavollita et al., *Circulation* 95(7): 1900–1909, 1997.

In addition, zsig37 polypeptides, fragments, fusions agonists or antagonists thereof may be therapeutically useful for anti-microbial or neurotransmitter-modulated applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial eridotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11): 933–41, 1993. Thus, soluble C1q-like molecules may be useful as anti-microbial agents, promoting lysis or phagocytosis of infectious agents.

The zsig37 polypeptides of the present invention also exhibit homology to moieties believed to modulate neurotransmission. As shown in FIG. 1, zsig37 polypeptides are homologous to the following proteins: HP25_TAMAS (Takamatsu et al., *Mol. Cell. Biol.* 13:1516–21, 1993 and Kondo & Kondo, *J. Biol. Chem.* 267:473–8, 1992); HP27_TAMAS (Takamatsu et al. and Kondo & Kondo referenced above) and CERL_RAT (Wada & Ohtani, *Brain Res. Mol. Brain Res.* 9:71–7, 1991). HP25 and HP27 are polypeptides found in the active (summer) serum of hibernating Siberian woodchucks. CERL is present in the rat cerebellum. Thus, zsig37 polypeptides, fragments, fusions, agonists or antagonists may be useful in modulating neurotransmission by, for example, binding to neurotransmitters or receptors therefor.

Radiation hybrid mapping is a somatic cell genetic technique developed for constructing high-resolution, contiguous maps of mammalian chromosomes (Cox et al., *Science* 250:245–250, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The results showed that the gene encoding the zsig37 polypeptide mapped to human chromosome 17, region 17q25.2, by PCR using the NIGMS Human/Rodent Somatic Cell Hybrid Mapping Panel Number 2 (National Institute of General Medical Sciences, Coriell Institute of Medical Research).

The present invention also provides reagents which will find use in diagnostic applications. For example, the zsig37 gene, a probe comprising zsig37 DNA or RNA, or a subsequence thereof can be used to determine if the zsig37 gene is present on chromosome 17 or if a mutation has occurred Detectable chromosomal aberrations at the zsig37 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

A condition associated with 17q25.2 is glycogen storage disease II. Thus, zsig37 polypeptide may be useful; in tile study, prevention or treatment, e.q., gene therapy, of this condition. If a mammal has a mutated or lacks a zsig37 gene, the zsig37 gene can be introduced into the cells of the mammal. In one embodiment, a gene encoding a zsig37 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector (Kaplitt et al., *Molec. Cell. Neurosci.*, 2:320–330 (1991)), an attenuated adenovirus vector, such as the vector described by Stratford-Perricaudet et al., *J. Clin. Invest.* 90:626–630 (1992), and a defective adeno-associated virus vector (Samulski et al., *J. Virol.*, 61:3096–3101 (1987); Samulski et al. *J. Virol.*, 63:3822–3828 (1989)).

In another embodiment, the gene can be introduced in a retroviral vector, e.g., as described in Anderson et al., U.S. Pat. No. 5,399,346; Mann et al., *Cell,* 33:153 (1983); Temin et al., U.S. Pat. No. 4,650,764; Temin et al., U.S. Pat. No. 4,980,289; Markowitz et al., *J. Virol.* 62:1120 (1988); Temin et al., U.S. Pat. No. 5,124,263; International Patent Publication No. WO 95/07358, published Mar. 16, 1995 by Dougherty et al.; and *Blood,* 82:845 (1993).

Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA,* 84:7413–7417 (1987); see Mackey et al., *Proc. Natl. Acad. Sci. USA,* 85:8027–8031 (1988)). The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–967 (1992); Wu et al., *J. Biol. Chem.* 263:14621–14624 (1988); and Johnston and Tang, *Methods in Cell Biology* 43:353–65 (1994).

Another aspect of the present invention involves antisense polynucleotide compositions that are complementary to a segment of the polynucleotides set forth in SEQ ID NO:1. Such synthetic antisense oligonucleotides are designed to bind to mRNA encoding zsig37 polypeptides and inhibit translation of such mRNA. Such antisense oligonucleotides are useful to inhibit expression of zsig37 polypeptide-encoding genes in cell culture or in a subject.

Zsig37 polypeptides may be used in the analysis of energy efficiency of a mammal. Zsig37 polypeptides found in serum or tissue samples may be indicative of a mammals ability to store food, with more highly efficient mammals tending toward obesity. More specifically, the present invention contemplates methods for detecting zsig37 polypeptide comprising:

exposing a sample possibly containing zsig37 polypeptide to an antibody attached to a solid support, wherein said antibody binds to an epitope of a zsig37 polypeptide;

washing said immobilized antibody-polypeptide to remove unbound contaminants;

exposing the immobilized antibody-polypeptide to a second antibody directed to a second epitope of a zsig37 polypeptide, wherein the second antibody is associated with a detectable label; and detecting the detectable label. The concentration of zsig37 polypeptide in the test sample appears to be indicative of the energy efficiency of a mammal. This information can aid nutritional analysis of a mammal. Potentially, this information may be useful in identifying and/or targeting energy deficient tissue.

Within additional aspects of the invention there are provided antibodies that specifically bind to the zsig37 polypeptides described above. Such antibodies are useful for, among other uses as described herein, preparation of anti-idiotypic antibodies. An additional aspect of the present invention provides methods for identifying agonists or antagonists of the zsig37 polypeptides disclosed above, which agonists or antagonists may have valuable properties as discussed further herein. Within one embodiment, there is provided a method of identifying zsig37 polypeptide agonists, comprising providing cells responsive thereto, culturing the cells in the presence of a test compound and comparing the cellular response with the cell cultured in the presence of the zsig37 polypeptide, and selecting the test compounds for which the cellular response is of the same type.

Within another embodiment, there is provided a method of identifying antagonists of zsig37 polypeptide, comprising providing cells responsive to a zsig37 polypeptide, culturing a first portion of the cells in the presence of zsig37 polypeptide, culturing a second portion of the cells in the presence of the zsig37 polypeptide and a test compound, and detecting a decrease in a cellular response of the second portion of the cells as compared to the first portion of the cells. In addition to those assays disclosed herein, samples can be tested for inhibition of zsig37 activity within a variety of assays designed to measure receptor binding or the stimulation/inhibition of zsig37-dependent cellular responses. For example, zsig37-responsive cell lines can be transfected with a reporter gene construct that is responsive to a zsig37-stimulated cellular pathway. Reporter gene constructs of this type are known in the art, and will generally comprise a zsig37-DNA response element operably linked to a gene encoding an assayable protein, such as luciferase. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56:563–72, 1989). Cyclic AMP response elements are reviewed in Roestler et al., *J. Biol. Chem.* 263(19):9063–6, 1988 and Habener, *Molec. Endocrinol.* 4(8):1087–94, 1990. Hormone response elements are reviewed in Beato, *Cell* 56:335–44; 1989. Candidate compounds, solutions, mixtures or extracts are tested for the ability to inhibit the activity of zsig37 on the target cells as evidenced by a decrease in zsig37 stimulation of reporter gene expression. Assays of this type will detect compounds that directly block zsig37 binding to cell-surface receptors, as well as compounds that block processes in the cellular pathway subsequent to receptor-ligand binding. In the alternative, compounds or other samples can be tested for direct blocking of zsig37 binding to receptor using zsig37 tagged with a detectable label (e.g., $^{125}$I, biotin, horseradish peroxidase, FITC, and the like). Within assays of this type, the ability of a test sample to inhibit the binding of labeled zsig37 to the receptor is indicative of inhibitory activity, which can be confirmed through secondary assays. Receptors used within binding assays may be cellular receptors or isolated, immobilized receptors.

A further aspect of the invention provides a method for studying insulin. Such methods of the present invention comprise incubating adipocytes in a culture medium comprising zsig37 polypeptide, monoclonal antibody, agonist or antagonist thereof±insulin and observing changes in adipocyte protein secretion or differentiation.

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial protective substances or the cell wall/membrane thereof. Anti-microbial agents, capable of inhibiting microorganism proliferation or action or of disrupting microorganism integrity by either mechanism set forth above, are useful in methods for preventing contamination in cell culture by microbes susceptible to that anti-microbial activity. Such techniques involve culturing cells in the presence of an effective amount of said zsig37 polypeptide or an agonist or antagonist thereof.

Also, zsig37 polypeptides or agonists thereof may be used as cell culture reagents in in vitro studies of exogenous microorganism infection, such as bacterial, viral or fungal infection. Such moieties may also be used in in vivo animal models of infection.

The present invention also provides methods of studying mammalian cellular metabolism. Such methods of the present invention comprise incubating cells to be studied, for example, human vascular endothelial cells, ±zsig37 polypeptide, monoclonal antibody, agonist or antagonist thereof and observing changes in adipogenesis, gluconeogenesis, glycogenolysis, lipogenesis, glucose uptake, or the like.

An additional aspect of the invention provides a method for studying dimerization or oligomerization. Such methods of the present invention comprise incubating zsig37 polypeptides or fragments or fusion proteins thereof containing a collagen-like domain alone or in combination with other polypeptides bearing collagen-like domains and observing the associations formed between the collagen like domains. Such associations are indicated by HPLC, circular dichroism or the like.

As previously noted, the isolated polynucleotides of the present invention include DNA and RNA. Methods for isolating DNA and RNA are well known in the art. It is generally preferred to isolate RNA from brain tumor, heart, placenta, adipose tissue and the like, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. Polynucleotides encoding zsig37 polypeptides are then identified and isolated by, for example, hybridization or PCR.

The present invention further provides counterpart polypeptides and polynucleotides from other species (orthologs or paralogs). These species include, but are not limited to mammalian, avian, amphibian, reptile, fish, insect and other vertebrate and invertebrate species. Of particular interest are zsig37 polypeptides from other mammalian species, including murine, rat, porcine, ovine, bovine, canine, feline, equine and other primate proteins. Orthologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A zsig37 polypeptide-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zsig37 polypeptide. Similar techniques can also be applied to the isolation of genomic clones. Orthologs can also be identified by screening species specific EST databases using the sequences provided herein. An EST encoding a murine zsig37 ortholog was found by screening a mouse EST database with as described in more detail below. The mouse ortholog (SEQ ID NO:43) has 77% identity with the human sequence at the nucleotide level and 7% identity at the amino acid level.

Those skilled in the art will recognize that the sequences disclosed in SEQ ID NO:1 and SEQ ID NO:2 represent a single allele of human zsig37 DNA and protein and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zsig37 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zsig37 polypeptides that are substantially homologous to the polypeptides of SEQ ID NO:2 and their species homologs/orthologs. The term "substantially homologous" is used herein to denote polypeptides having 50%, preferably 60%, more preferably at least 80%, sequence identity to the sequences shown in SEQ ID NO:2 or their orthologs or paralogs. Such polypeptides will more preferably be at least 90% identical, and most preferably 95% or more identical to SEQ ID NO:2 or its orthologs or paralogs. Percent sequence identity is determined by conventional methods. See, for example, Altschul et al., *Bull. Math. Bio.* 48:603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxy-proline, trans-4-hydroxyproline, N-methylglycine, allo-threonine, methylthreonine, hydroxyethylcysteine, hydroxyethylhomocysteine, nitroglutamine, homoglutamine, pipe-

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the zsig37 polypeptide and the affinity tag. Preferred such sites include thrombin cleavage sites and factor Xa cleavage sites.

colic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al.,

*Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zsig37 amino acid residues.

Essential amino acids in the polypeptides of the present invention can be identified according to procedures known in the art, such as site-directed mutagenesis or alanine-scanning mutagenesis (Cunningham and Wells, *Science* 244:1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity (e.g., ability to modulate energy balance) as disclosed below to identify amino acid residues that are critical to the activity of the molecule. See also, Hilton et al., *J. Biol. Chem.* 271:4699–708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–12, 1992; Smith et. al., *J. Mol. Biol.* 224:899–904, 1992; Wlodaver et al., *FEBS Lett.* 309:59–64, 1992. The identities of essential amino acids can also be inferred from analysis of homologies with related polypeptides.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zsig37 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., ability to modulate energy balance) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 22 to 281 of SEQ ID NO:2 or allelic variants thereof and retain the energy balance modulating or other properties of the wild-type protein. Such polypeptides may include additional amino acids, such as additional collagen repeats of the Gly-Xaa-Pro or Gly-Xaa-Xaa type. Such polypeptides may also include additional polypeptide segments as generally disclosed above.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al. (eds.), *Current Protocols in Molecular Biology,* John Wiley and Sons, Inc., NY, 1987.

In general, a DNA sequence encoding a zsig37 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig37 polypeptide into the secretory pathway of a host cell, a secretory signal sequence (also known as a leader sequence, signal sequence, prepro sequence or pre sequence) is provided in the expression vector. The secretory signal sequence may be that of the zsig37 polypeptide, or may be derived from another secreted protein (e.g., t-PA) or synthesized de novo. The secretory signal sequence is joined to the zsig37 polypeptide DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Conversely, the signal sequence portion of the zsig37 polypeptide (amino acids 1–21 or 1–25 of SEQ ID NO:2) may be employed to direct the secretion of an alternative protein by analogous methods.

The secretory signal sequence contained in the polypeptides of the present invention can be used to direct other polypeptides into the secretory pathway. The present invention provides for such fusion polypeptides. A signal fusion polypeptide can be made wherein a secretory signal sequence derived from amino acid residues 1–22 or 1–25 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are also suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), liposome-mediated transfection (Hawley-Nelson et al., *Focus* 15:73, 1993; Ciccarone et al., *Focus* 15:80, 1993), and viral vectors (A. Miller and G. Rosman, *BioTechniques* 7:980–90, 1989; Q. Wang and M. Finer, *Nature Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573;. Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zsig37 baculovirus utilizes a transposon-based system described by Luckow (Luckow et al., *J. Virol.* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zsig37 polypeptide into a baculovirus genome maintained in *E. coli* as a large plasmid called a "bacmid." See, Hill-Perkins and Possee, *J. Gen. Virol.* 71:971–6, 1990; Bonning et al., *J. Gen. Virol.* 75:1551–6, 1994; and, Chazenbalk and Rapoport, *J. Biol. Chem.* 270:1543–9, 1995. In addition, transfer vectors can include an in-frame fusion with DNA encoding an epitope tag at the C- or N-terminus of the expressed zsig37 polypeptide, for example, a Glu-Glu epitope tag (Grussenmeyer et al., *Proc. Natl. Acad. Sci.* 82:7952–4, 1985). Using a technique known in the art, a transfer vector containing zsig37 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig37 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King and Possee, ibid.; O'Reilly et al., ibid.; Richardson, ibid.). Subsequent purification of the zsig37 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig37 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered, and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant zsig37 polypeptides (or chimeric zsig37 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural or binding properties. For example, immobilized metal ion adsorption (IMAC) chromatography can be used to purify histidine-rich proteins or proteins having a His tag. Briefly, a gel is first charged with divalent metal ions to form a chelate (E. Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within an additional preferred embodiments of the invention, a fusion of the polypeptide of interest and an affinity tag (e.g., maltose-binding protein, FLAG, Glu-Glu, an immunoglobulin domain) may be constructed to facilitate purification as is discussed in greater detail in the Example sections below.

Protein refolding (and optionally, reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zsig37 polypeptides or fragments thereof may also be prepared through chemical synthesis. Such zsig37 polypeptides may be monomers or multimers; glycosylated or non-glycosylated; pegylated or non-pegylated; and may or may not include an initial methionine amino acid residue.

A ligand-binding polypeptide, such as a zsig37 polypeptide-binding polypeptide, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the ligand-binding polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding polypeptides can also be used within other assay systems known in the art. Such systems include Scatchard analysis for determination of binding affinity (see Scatchard, *Ann. NY Acad. Sci.* 51:660–72, 1949) and calorimetric assays (Cunningham et al., *Science* 253:545–48, 1991; Cunningham et al., *Science* 245:821–25, 1991).

Zsig37 polypeptides can also be used to prepare antibodies that specifically bind to zsig37 polypeptide epitopes, peptides or polypeptides. Methods for preparing polyclonal and monoclonal antibodies are well known in the art (see, for example, Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982).

As would be evident to one of ordinary skill in the art, polyclonal antibodies can be generated from inoculating a variety of warm-blooded animals such as horses, cows, goats, sheep, dogs, chickens, rabbits, mice, hamsters, guinea pigs and rats as well as transgenic animals such as transgenic sheep, cows, goats or pigs. Antibodies may also be expressed in yeast and fungi in modified forms as well as in mammalian and insect cells. The zsig37 polypeptide or a fragment thereof serves as an antigen (immunogen) to inoculate an animal or elicit an immune response. Suitable antigens would include the zsig37 polypeptide encoded by SEQ ID NO:2 from amino acid residue 22–281 of SEQ ID NO:2, from amino acid residue 26–281 of SEQ ID NO:2, or a contiguous 9–281 amino acid residue fragment thereof. The immunogenicity of a zsig37 polypeptide may be increased through the use of an adjuvant, such as alum (aluminum hydroxide) or Freund's complete or incomplete adjuvant. Polypeptides useful for immunization also include fusion polypeptides, such as fusions of zsig37 or a portion thereof with an immunoglobulin polypeptide or with an affinity tag. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zsig37 protein or peptide, and selection of antibody display libraries in phage or similar vectors (for instance, through use of immobilized or labeled zsig37 protein or peptide).

Antibodies are defined to be specifically binding if: 1) they exhibit a threshold level of binding activity, and/or 2) they do not significantly cross-react with related polypeptide molecules. First, antibodies herein specifically bind if they bind to a zsig37 polypeptide, peptide or epitope with a binding affinity ($K_a$) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (Scatchard, *Ann. NY Acad. Sci.* 51:660–672, 1949).

Second, antibodies specifically bind if they do not significantly cross-react with related polypeptides. Antibodies do not significantly cross-react with related polypeptide molecules, for example, if they detect zsig37 polypeptide but not known related polypeptides using a standard Western blot analysis (Ausubel et al., ibid.). Examples of known related polypeptides include other members of a protein family such as Acrp30 (SEQ ID NO:3), the polypeptides shown in alignment FIG. 1 and the like. They could also include, if desired, orthologs and mutant human zsig37 polypeptides. Moreover, antibodies may be "screened against" known related polypeptides to isolate a population that specifically binds to the inventive polypeptides. For example, antibodies raised to human zsig37 polypeptides are adsorbed to related polypeptides adhered to insoluble matrix; antibodies specific to human zsig37 polypeptides will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art (see, *Fundamental Immunology*, Paul (eds.), Raven Press, 1993; Getzoff et al., *Adv. in Immunol.* 43:1–98, 1988; *Monoclonal Antibodies: Principles and Practice*, Goding, J. W. (eds.), Academic Press Ltd., 1996; Benjamin et al., *Ann. Rev. Immunol.* 2:67–101, 1984). Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay.

Genes encoding polypeptides having potential zsig37 polypeptide binding domains, "binding proteins", can be obtained by screening random or directed peptide libraries displayed on phage (phage display) or on bacteria, such as *E. coli*. Nucleotide sequences encoding the polypeptides can be obtained in a number of ways, such as through random mutagenesis and random polynucleotide synthesis. Alternatively, constrained phage display libraries can also be produced. These peptide display libraries can be used to screen for peptides which interact with a known target which can be a protein or polypeptide, such as a ligand or receptor, a biological or synthetic macromolecule, or organic or inorganic substances. Techniques for creating and screening such peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Peptide display libraries can be screened using the zsig37 sequences disclosed herein to identify proteins which bind to zsig37. These "binding proteins" which interact with zsig37 polypeptides can be used essentially like an antibody, for tagging cells; for isolating homolog polypeptides by affinity purification; directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. To increase the half-life of these binding proteins, they can be conjugated. Their biological properties may be modified by dimerizing or multimerizing for use as agonists or antagonists. Binding peptides can be screened against known related polypeptides as described above.

Antibodies and binding proteins to zsig37 may be used for tagging cells that express zsig37; for isolating zsig37 by affinity purification; for diagnostic assays for determining circulating levels of zsig37 polypeptides; for detecting or quantitating soluble zsig37 as marker of underlying pathology or disease; in analytical methods employing FACS; for screening expression libraries; for generating anti-idiotypic antibodies; and as neutralizing antibodies or as antagonists to block zsig37 polypeptide energy balance modulation activity or like activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Moreover, antibodies to zsig37 or fragments thereof may be used in vitro to detect denatured zsig37 or fragments thereof in assays, for example, Western Blots or other assays known in the art.

Antibodies or binding proteins herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zsig37 polypeptides or anti-zsig37 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anticomplementary molecule can be conjugated to a detectable or cytotoxic molecule. Such domain-complementary molecule fusion proteins thus represent a generic targeting vehicle for cell/tissue-specific delivery of generic anticomplementary-detectable/cytotoxic molecule conjugates. The bioactive polypeptide or antibody conjugates described herein can be delivered intravenously, intraarterially, intraductally with DMSO, intramuscularly, subcutaneously, intraperitoneally, also by transdermal methods, by electro-transfer, orally or via inhalant.

Polynucleotides encoding zsig37 polypeptides are useful within gene therapy applications where it is desired to increase or inhibit zsig37 activity. If a mammal has a mutated or absent zsig37 gene, the zsig37 gene can be introduced into the cells of the mammal. In one embodiment, a gene encoding a zsig37 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors, allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zsig37 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; WIPO Publication WO 95/07358; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e g., Wu et al., *J. Biol. Chem.* 267:963–7, 1992; Wu et al., *J. Biol. Chem.* 263:14621–4, 1988.

Antisense methodology can be used to inhibit zsig37 gene transcription, such as to inhibit cell proliferation in vivo. Polynucleotides that are complementary to a segment of a zsig37-encoding polynucleotide (e.g., a polynucleotide as set froth in SEQ ID NO:1) are designed to bind to zsig37-encoding mRNA and to inhibit translation of such mRNA. Such antisense polynucleotides are used to inhibit expression of zsig37 polypeptide-encoding genes in cell culture or in a subject.

Transgenic mice, engineered to express the zsig37 gene, and mice that exhibit a complete absence of zsig37 gene function, referred to as "knockout mice" (Snouwaert et al., *Science* 257:1083, 1992), may also be generated (Lowell et al., *Nature* 366:740–42, 1993). These mice may be employed to study the zsig37 gene and the protein encoded thereby in an in vivo system.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig37 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton Pa., 19$^{th}$ ed., 1995. Therapeutic doses will generally be determined by the clinician according to accepted standards, taking into account the nature and severity of the condition to be treated, patient traits, etc. Determination of dose is within the level of ordinary skill in the art.

The invention is further illustrated by the following non-limiting examples.

EXAMPLE 1

Extension of EST Sequence

The novel zsig37 polypeptide-encoding polynucleotides of the present invention were initially identified by selecting an EST from an EST database, predicting a protein sequence based thereupon, and searching known sequence databases for the secreted protein that is most homologous to predicted protein based on the EST. ESTs that potentially encode proteins having biologically interesting homology to known secreted proteins were identified for further study. A single EST sequence was discovered and predicted to be homologous to adipocyte specific protein. See, for example, Scherer et al., J. Biol. Chem. 270(45): 26746–9, 1995. To identify the corresponding cDNA, a clone considered likely to contain the entire coding sequence was used for sequencing. Using an Invitrogen S.N.A.P.O Miniprep kit (Invitrogen, Corp., San Diego, Calif.) according to manufacturer's instructions a 5 ml overnight culture in LB 50 mg/ml ampicillin was prepared. The template was sequenced on an ABIPRISM C) model 377 DNA sequencer (Perkin-Elmer Cetus, Norwalk, Ct.) using the ABI PRISM6 Dye Terminator Cycle Sequencing Ready Reaction Kit (Perkin-Elmer Corp.) according to manufacturer's instructions. Oligonucleotides ZC695 (SEQ ID NO:5), ZC694 (SEQ ID NQ:6) to the SP6 and Ti promoters on the clone-containing vector were used as sequencing primers. Oligonucleotides ZC 13210 (SEQ ID NO:7), ZC13588 (SEQ ID NO:8), ZC13532 (SEQ ID NO:9), ZC13641 (SEQ ID NO:10), ZC13586 (SEQ ID NO:11), ZC13651 (SEQ ID NO:12), ZC13622 (SEQ ID NO:13), ZC13625 (SEQ ID NO:14), ZC13650 (SEQ ID NO:15), ZC13589 (SEQ ID NO:16), ZC13624 (SEQ ID NO:17), ZC13531 (SEQ ID NO:18), ZC13587 (SEQ ID NO:19), and ZC 13623 (SEQ ID NO:20) were used to complete the sequence from the clone. Sequencing reactions were carried out in a HYBAID OMNIGENE Temperature Cycling System (National Labnet Co., Woodbridge, NY). SEQUENCHERÔ 3.0 sequence analysis software (Gene Codes Corporation, Ann Arbor, Mich.) was used for data analysis. The resulting 2769 bp sequence is disclosed in SEQ ID NO: 1. Comparison of the originally derived EST sequence with the sequence represented in SEQ ID NO:1 showed that there was one base pair ambiguity (an unknown "N" residue) and no base pair insertions which resulted in the identification of leucine in resolution of the ambiguity and zero frame shifts between the deduced amino acid sequences.

EXAMPLE 2

Tissue Distribution

Northerns were performed using Human Multiple Tissue Blots from Clontech (Palo Alto, Calif.). A 30 base DNA probe (ZC12447; SEQ ID NO:4) to the 5' end of the nucleotide sequence of the mature protein shown in SEQ ID NO: 1 was radioactively labeled with32P using T4 polynucleotide kinase and FORWARD REACTION BUFFER (GIBCO BRL, Gaithersburg, Md.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 50° C., and the blots were then washed in 2×SSC and 0.1% SDS at RT, followed by a wash in iX SSC and 0.1% SDS at 680C (about 5° C. less than the melting point). One transcript size was observed at approximately 2.8 kb. Signal intensity was highest for heart and placenta, with relatively less intense signals in kidney, ovary, adrenal gland and skeletal muscle and lower signals in a wide variety of other tissues present on the Northern blot.

Additional Northern Blot Analysis was done using a Gut Northern Tissue Blot. The blot was prepared using mRNA from human colorectal adenocarcinoma cell line SW480 (Clontech, Palo Alto, Calif.), human small intestine tissue (Clontech), human stomach tissue (Clontech), human intestinal smooth muscle cell line (Hism; ATCC No.CRL-1692; American Type Culture Collection, 12301 Parklawn Drive, Rockville, Md.), normal human colon cell line (FHC; ATCC No. CRL-1831; American Type Culture Collection) and human normal fetal small intestine cell line (FHs74 Int.; ATCC No. CCL241; American Type Culture Collection).

Total RNAs were isolated from Hism, FHC and FHs74 Int. by acid guanidium method (Cheomczynski et al., Anal. Biochem. 162:156–9, 1987). The polyA RNAs were selected by eluting total RNA through a column that retains polyA RNAs (Aviv et al., Proc. Nat. Acad. Sci. 69:1408–12, 1972). 2 mg of polyA+ RNA from each sample was separated out in a 1.5% agarose gel in 2.2 M formaldehyde and phosphate buffer. The RNAs were transferred onto NYTRAN membrane (Schleicher and Schuell, Keene, NH) in 20×SSC overnight. The blot was treated in the UV STRATAUINKER 2400 (Stratagene, La Jolla, Calif.) at 0.12 Joules. The bolt was then baked at 80° C. for one hour.

Full length cDNA (shown in SEQ ID NO:1) was amplified by PCR and radiolabeled with $^{32}$P dCTP using a REDIPRIME pellet kit (Amersham, Arlington Heights, Ill.) according to the manufacturer's specifications. The blot was hybridized in EXIPRESSHYB (Clontech) at 56° C. overnight. The blot was washed at room temperature in 2×SSC and 0.1% SDS, then in 2×SSC and 0.1% SDS at 65° C., and finally at 65° C. in 0.1×SSC and 0.1% SDS. Results showed that zsig37 hybridized to all tissues except the human intestinal smooth muscle cell line HISM.

EXAMPLE 3

Chromosomal Mapping of the Zsiq37 Gene

The zsig37 gene was mapped to human chromosome 17, region 17q25.2, by PCR using the NIGMS Human/Rodent Somatic Cell Hybrid Mapping Panel Number 2 (National Institute of General Medical Sciences, Conch Institute of Medical Research). The panel consists of DNA isolated from 24 human/rodent somatic cell hybrids each retaining one specific human chromosome and the parental DNAs. For the mapping of the zsig37 gene, 20 µl reactions were set up in a 96-well microtiter plate (Stratagene, La Jolla, Calif.) and used in a "RoboCycler Gradient 96" thermal cycler (Stratagene). Each of the 27 PCR reactions consisted of 2 µl 10×KLENTAO PCR reaction buffer (Clontech Laboratories, Inc., Palo Alto, Calif.), 1.6 µl dNTPs mix (2.5 mM each, PERKIN-ELMER, Foster City, Calif.), 1 µl sense primer (SEQ ID NO:21), 1 µl antisense primer(SEQ ID NO:22), 2 µl REDILOAD (Research Genetics, Inc.), 0.4 µl 50×Advantage KLENTAO Polymerase Mix (Clontech Laboratories, Inc.), 25 ng of DNA from an individual hybrid clone or control and ddH2O for a total volume of 20 µl. The reactions were overlaid with an equal amount of mineral oil and sealed. The PCR cycler conditions were as follows: an initial I cycle 5 minute denaturation at 95° C., 35 cycles of a 1 minute denaturation at 95° C., 1 minute annealing at 60° C. and 1.5 minute extension at 72° C., followed by a final 1 cycle extension of 7. minutes at 72° C. The reactions were separated by electrophoresis on a 3% NUSLEVE GTG agarose gel (FMC Bioproducts, Rockland, Me.).

EXAMPLE 4

Creation of Mammalian Expression Vectors zsig37NEE/pZP9 and zsig37CEE/pZP9

Two expression vectors were prepared for the zsig37 polypeptide, zSIG37NEE/pZP9 and zSIG37CEE/pZP9, wherein the constructs were designed to express a zsig37 polypeptide having a C- or N-terminal Glu-Glu tag.

Zsig37NEE/pZP9

A 800 bp PCR generated zsig-37 DNA fragment was created using ZC15040 (SEQ ID NO:24) and ZC15033 (SEQ ID NO:25) as PCR primers and the template described in Example 1 above. The PCR reaction was incubated at 94° C. for 3 minutes, and then run for 5 cycles of 94° C. for 30 seconds, 30° C. for 20 seconds and 72° C. for 1 minute, followed by 25 cycles at 94° C. for 30 seconds, 64° C. for 20 seconds and 72 C for 1 minute. A 5 minute extension at 72° C. followed. The resultant PCR product was then run on a 0.9% TBE agarose gel with 1×TBE buffer. A band of the predicted size was excised and the DNA was purified from the gel with a Qiaex II® resin (Qiagen) according the manufacturer's instructions. The DNA was digested with the restriction enzymes Bam HI and Xba I, followed by extraction and precipitation.

The excised, restriction digested zsig37 DNA fragment was subcloned into plasmid NEE/pZP9 which had been cut with the restriction enzymes Bam HI and Xba I. The zsig37NEE/pZP9 expression vector incorporates the TPA leader and attaches a Glu-Glu tag (SEQ ID NO:26) to the N-terminal of the zsig37 polypeptide-encoding polynucleotide sequence. Plasmid NEE/pZP9 (deposited at the American Type Culture Collection, 12301 Parklawn Drive, Rockville, Md., ATCC No. 98668) is a mammalian expression vector containing an expression cassette having the mouse metallothionein-1 promoter, a TPA leader peptide followed by the sequence encoding the Glu-Glu tag (SEQ ID NO:26), multiple restriction sites for insertion of coding sequences, and a human growth hormone terminator. The plasmid also contains an E. coli origin of replication, a mammalian selectable marker expression unit having an SV40 promoter, enhancer and origin of replication, a DHFR gene and the SV40 terminator.

zsig376CEE/pZP9

A 866 bp PCR generated zsig37 DNA fragment was created in accordance with the procedure set forth above using ZC15721 (SEQ ID NO:27) and ZC15035 (SEQ ID NO:28) as PCR primers. The purified PCR fragment was digested with the restriction enzymes Eco RI and Bam HI, gel purified using a Qiaex II resin as described above.

The excised and restriction digested zsig37 DNA was subcloned into plasmid CEE/pZP9 which had been cut with Eco RI and Bam HI. The zsig37CEE/pZP9 expression vector uses the native zsig37 signal peptide, and the Glu-Glu epitope (SEQ ID NO:26) is attached at the C-terminus as a purification aid. Plasmid CEE/pZP9 (deposited at the American Type Culture Collection, 12301 Parklawn Drive, Rockville, Md., ATCC No. 98668) is a mammalian expression vector containing an expression cassette having the mouse metallothionein-1 promoter, multiple restriction sites for insertion of coding sequences, a sequence encoding the Glu-Glu tag (SEQ ID NO:26), a stop codon and a human growth hormone terminator. The plasmid also has an E. coli origin of replication, a mammalian selectable marker expression unit having an SV40 promoter, enhancer and origin of replication, a DHFR gene and the SV40 terminator.

For the N- and C-tagged constructs, about 30 ng of the restriction digested inserts and 50 ng of the corresponding vectors were ligated at room temperature for 4 hours. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight.

Colonies were screened by PCR as described above. For zsig37NEE/pZP9 and zsig37CEE/pZP9 screens the primers were ZC13006 (SEQ ID NO:29) and ZC13007 (SEQ ID NO:20). The PCR reaction was incubated at 94° C. for 2.5 minutes, and then run for 25 cycles of 94° C. for 10 seconds, 58° C. for 20 seconds and 72° C. for 1 minute. A 5 minute extension at 72° C. followed. The insert sequence of positive clones, 1013 bp for zsig37NEE and a 950 bp fragment for zsig37CEE were verified by sequence analysis. A large scale plasmid preparation was done using a QIAGEN® Maxi prep kit (Qiagen) according to manufacturer's instructions.

EXAMPLE 5

Transfection and Expression of zsig37NEE and CEE Polypeptides

BHK 570 cells (ATCC No. CRL-10314) were plated in 10 cm tissue culture dishes and allowed to grow to approximately 50 to 70% confluency overnight at 37° C., 5% $CO_2$, in DMEM/FBS media (DMEM, Gibco/BRL High Glucose, (Gibco BRL, Gaithersburg, Md.), 5% fetal bovine serum (Hyclone, Logan, Utah), 2 µM L-glutamine (JRH Biosciences, Lenexa, Kans.), 1 µM sodium pyruvate (Gibco BRL)). The cells were then transfected with the plasmid zsig37NEE/pZP9 (N-terminal Glu-Glu tag) or zsig37CEE/pZP9 (C-terminal Glu-Glu tag), using Lipofectamine™ (Gibco BRL), in serum free (SF) media formulation (DMEM, Gibco/BRL High Glucose, (Gibco BRL, Gaithersburg, Md.), 2 mM L-glutamine, 2 mM sodium pyruvate, 10 ug/ml transferrin, 5 µg/ml insulin, 10 µg/ml fetuin and 2 ng/ml selenium). Sixteen micrograms of zsig37NEE/pZP9 and 16 µg of zsig37CEE/pZP9 were separately diluted into 15 ml tubes to a total final volume of 640 µl SF media. In separate tubes, 35 µl of Lipofectamine™ (Gibco BRL) was mixed with 605 µl of SF medium. The Lipofectamine™ mix was added to the DNA mix and allowed to incubate approximately 30 minutes at room temperature. Five milliliters of SF media was added to the DNA:Lipofectamine™ mixture. The cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to the plate. The plate was incubated at 37° C. overnight and the DNA:Lipofectamine™ mixture was replaced with fresh FBS/DMEM media the next day. On day 2 post-transfection, the cells were split into the selection media (ESTEP #1 with 1 µM MTX) in 150 mm plates at 1:50, 1:100 and 1:200. The plates were refed at day 5 post-transfection with fresh selection media.

Screening Colonies

Approximately 10–12 days post-transfection, one 150 mm culture dish of methotrexate resistant colonies was chosen from each transfection, the media aspirated, the plates washed with 10 ml serum-free ESTEP 2 media (668.7g/50L DMEM (Gibco), 5.5 g/50L pyruvic acid, sodium salt 96% (Mallinckrodt), 185.0 g/50L NaHCO3 (Mallinkrodt), 5.0 mg/ml, 25 mlI50L insulin, 10.0 mg/ml and 25 ml/50 L transferrin). The wash media was aspirated and replaced with 5 ml serum-free ESTEP 2. Sterile TEFLON mesh (Spectrum Medical Industries, Los Angeles, Calif.) pre-soaked in serum-free ESTEP 2 was then placed over the cells. A sterile nitrocellulose filter pre-soaked in serum-free ESTEP 2 was then placed over the mesh. Orientation marks on the nitrocellulose were transferred to the culture dish. The plates were then incubated for 5–6 hours in a 37° C., 5% $CO_2$ incubator. Following incubation, the filter was removed, and the media aspirated and replaced with DMEMI5% FBS, 1×PSN (Gibco BRL) media. The filter was then placed into a sealable bag containing 50 ml buffer (25 mM Tris, 25 mM glycine, 5 mM b-mercaptoethanol) and incubated in a 65° C. water bath for 10 minutes. The filters were blocked in 10% nonfat dry milk/Western A buffer (Western A: 50 mM Tris pH 7.4, 5 mM EDTA, 0.05% NP-40, 150 mM NaCl and 0.25% gelatin) for 15 minutes at room temperature on a rotating shaker. The filter was then incubated with an anti-Glu-Glu antibody-HRP conjugate at a 1:1000 dilution in 2.5% nonfat dry milk/Western A buffer (Western A: 50 mM Tris pH 7.4, 5 mM EDTA, 0.05% NP-40, 150 mM NaCl and 0.25% gelatin) overnight at 4° C. on a rotating shaker. The filter was then washed three times at room temperature in PBS plus 0.1% Tween 20, 5–15 minutes per wash. The filter was developed with ECL reagent (Amersham Corp., Arlington Heights, IL) according the manufacturer's directions and exposed to film HYPERFILM ECL, Amersham) for approximately 5 minutes.

The film was aligned with the plate containing the colonies. Using the film as a guide, suitable colonies were selected. Sterile, 3 mm coloning discs (PGC Scientific Corp., Frederick, Md.) were soaked in trypsin, and placed on the colonies. Twelve colonies for each construct were transferred into 200 µl of selection medium in a 96 well plate. A series of seven, two-fold dilutions were carried out for each colony. The cells were grown for one week at 37° C. at which time the wells which received the lowest dilution of cells which are now at the optimum density were selected, trypsinized and transferred to a 12 well plate containing selection media. The 150 mm culture dish was also trypsinized and the remainder of the cells were pooled and subjected to western analysis and mycoplasma testing. The pool was frozen for storage.

The clones were expanded directly from the 12 well plate into two T-75 flasks. One flask was kept to continue cell growth, the second flask was grown in serum-free ESTEP 2 which was harvested for Western Blot analysis. Clones of each of the expression constructs, based on Western blot analysis, were selected, pooled and transferred to large scale culture.

EXAMPLE 7

Large Scale Mammalian Expression of zsig37CEE

One T-162 flask, containing confluent cells expressing zsig37CEE and one containing zsig37NEE obtained from the expression procedure described above, were expanded into four T-162 flasks each. One of the four resulting flasks was used to freeze down four cryovials, and the other three flasks were used to generate a Nunc cell factory.

The cells from the three T-162 flasks of zsig37CEE and zsig37NEE were used to independently seed two Nunc cell factories (10 layers, commercially available from VWR). Briefly, the cells from the T-162 flasks described above were detached using trypsin, pooled, and added to 1.5 liters ESTEP1 media (668.7 g/50L DMEM (Gibco), 5.5 g/50L pyruvic acid, sodium salt 96% (Mallinckrodt), 185.0 g/50L $NaHCO_3$ (Mallinkrodt), 5.0 mg/ml and 25 ml/50L insulin (JRH Biosciences), 10.0 mg/ml and 25 ml/50L transferrin (JRH Biosciences), 2.5L/50L fetal bovine serum (characterized) (Hyclone), 0.1 µM MTX, with pH adjusted to 7.05+/−0.05) prewarmed to 37° C. The media containing the cells was then poured into the Nunc cell factories via a funnel. The cell factories were placed in a 37° C./5.0% $CO_2$ incubator.

At 80–100% confluence, a visual contamination test (phenol red color change) was performed on the contents of the Nunc cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 5 to 10 minutes in the residual trypsin. The cells were collected following two, 200 ml washes with ESTEP1 media. To each of ten ESTEP1 media-containing bottles (1.5 liters each, at 37° C.) was added 40 mls of collected cells. One 1.5 liter bottle was then used to fill one Nunc factory. Each cell factory was placed in a 37° C./5.0% $CO_2$ incubator.

At 80–90% confluence, a visual contamination test (phenol red color change) was performed on the Nunc cell factories. Since no contamination was observed, supernatant from the confluent factories was poured into a small harvest container, sampled and discarded. Cells were then washed once with 400 ml PBS. 1.5 liters of ESTEP2 media (668.7 g/50L DMEM (Gibco), 5.5 g/50L pyruvic acid, sodium salt 96% (Mallinckrodt), 185.0 g/50L $NaHCO_3$ (Mallinkrodt), 5.0 mg/ml, 25 ml/50L insulin, 10.0 mg/ml and 125 ml/50L transferrin) was added to each Nunc cell factory. The cell factories were incubated at 37° C./5.0% $CO_2$.

At approximately 48 hours a visual contamination test (phenol red color change) was performed on the Nunc cell factories. Supernatant from each factory was poured into small harvest containers. Fresh serum-free media (1.5 liters) was poured into each Nunc cell factory, and the factories were incubated at 37° C./5.0% $CO_2$. One ml of supernatant harvest for each construct was transferred to a microscope slide, and subjected to microscopic analysis for contamination. The contents of the small harvest containers for each construct were pooled and immediately filtered. A second harvest was then performed, substantially as described above at 48 hours and the cell factories were discarded thereafter. An aseptically assembled filter train apparatus was used for aseptic filtration of the harvest supernatant (conditioned media). Assembly was as follows: tubing was wire-tied to an OPTI-CAP filter (Millipore Corp., Bedford, Mass.) and a GELMAN SUPERCAP 50 filter (Gelman Sciences, Ann Arbor, Mich.). The SUPERCAP 50 filter was also attached to a sterile capped container located in a hood; tubing located upstream of the Millipore OPTI-CAP filter was inserted into a peristaltic pump; and the free end of the tubing was placed in the large harvest container. The peristaltic pump was run between 200 and 300 rpm, until all of the conditioned media passed through the 0.22 mm final filter into a sterile collection container. The filtrate was placed in a 4° C. cold room pending purification. The media was concentrated 10× with a Millipore 5 kDA cut off concentrator (Millipore Corp., Bedford, Mass.) according to manufacturer's direction and subjected to Western Blot analysis using an anti-FLAG tag antibody (Kodak).

Zsiq37CEE:

5 T-162 Flasks=0.12 mg/L, 38 kDa;

1 Factory, FBS=0.12 mg/L, 38 kDa;

10 Factories, FBS=0.12 mg/L, 38 kDa;

10 Factories (#1), SF=1.2 mg/L, 38 kDa; and

10 Factories (#2), SF=3.56 mg/L, 38 kDa

Zsig37NEE:

5 T-162 Flasks=0.137 mg/L, 35 kDa;

1 Factory, FBS=0.137 mg/L, 35 kDa;

10 Factories, FBS=0.137 mg/L, 35 kDa;

10 Factories (#1), SF=1.37 mg/L, 35 kDa; and

10 Factories (#2), SF=4.11 mg/L, 35 kDa.

EXAMPLE 7

Purification of zsig37 NEE and zsig37 CEE

Unless otherwise noted, all operations were carried out at 4° C. The following procedure was used for purifying zsig37 containing N-terminal or C-terminal Glu-Glu (EE) tags. A total of 25 liters of conditioned media from baby hamster kidney (BHK) cells was sequentially sterile filtered through a 4 inch, 0.2 mM Millipore (Bedford, Mass.) OPTICAP capsule filter and a 0.2 mM GELMAN (Ann Arbor, Mich.) SUPERCAP 50. The material was then concentrated to about 1.3 liters using a Millipore PROFLUX A30 tangential flow concentrator fitted with a 3000 kDa cutoff Amicon (Bedford, Mass.) S 10Y3 membrane. The concentrated material was again sterile-filtered with the Gelman filter as described above. A mixture of protease inhibitors was added to the concentrated conditioned media to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM PEFABLOC (Boebringer-Mannheim). A 25.0 ml sample of anti-EE Sepharose, prepared as described below, was added to the sample for batch adsorption and the mixture was gently agitated on a Wheaton (Miliville, NJ) roller culture apparatus for 18.0 h at 4° C.

The mixture was then poured into a 5.0×20.0 cm ECONO—COLUMN (Bio-Rad, Laboratories, Hercules, Calif.) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed batch-wise with 2.0 column volumes of PBS containing 0.4 mg/ml of EE peptide (AnaSpec, San Jose, Calif.). The peptide used has the sequence Glu-Tyr-Met-Pro-Val-Asp, SEQ ID NO:31). After 1.0 h at 4° C., flow was resumed and the eluted protein was collected. This fraction was referred to as the peptide elution. The anti-EE Sepharose gel was then washed with 2.0 column volumes of 0.1 M glycine, pH 2.5, and the glycine wash was collected separately. The pH of the glycine-eluted fraction was adjusted to 7.0 by the addition of a small volume of lox PBS and stored at 4° C. for future analysis if needed.

The peptide elution was concentrated to 5.0 ml using a 15,000 molecular weight cutoff membrane concentrator (Millipore, Bedford, Mass.) according to the manufacturer's instructions. The concentrated peptide elution was separated from free peptide by chromatography on a 1.5×50 cm SEPHADEX G-50 (Pharmacia, Piscataway, N.J.) column equilibrated in PBS at a flow rate of 1.0 ml/mm using a BIOCAD Sprint HPLC (PerSeptive RioSystems, Framingham, MA). Two-ml fractions were collected and the absorbance at 280 nM was monitored. The first peak of material absorbing at 280 nM and eluting near the void volume of the column was collected. This fraction was pure zsig37 NEE or zsig37 GEE. The pure material was concentrated as described above, analyzed by SDS-PAGE and Western blotting with anti-EE antibodies, and samples were taken for amino acid analysis and N-terminal sequencing. The remainder of the sample was aliquoted, and stored at −80° C. according to our standard procedures.

Electrophoresis of zsig37 NEE on SDS-PAGE gels in the absence of reducing agents, showed one major Coomassie Blue-stained band of apparent molecular weight 39,000 and several minor components of molecular weights between 60,000 and 116,000. All of the bands showed cross reactivity with anti-EE antibodies on Western blots. In the presence of reducing agent, the only band observed was the 39,000 kDa protein, and its Coomassie Blue staining intensity was increased. This band also showed cross-reactivity with the anti-EE antibody on Western blots.

For zsig37 CEE, electrophoresis on SDS-PAGE gels in the absence of reducing agents showed one major Coomassie Blue-stained band of apparent molecular weight 39,000 and several minor components of molecular weights between 60,000 and 116,000. On Western blots, only bands of apparent molecular weights 150,000, 116,000, and 60,000 showed cross-reactivity with the anti-EE antibody. In the presence of reducing agents, only the Coomassie Blue-stained band at 39,000 kDa was observed and this material showed cross-reactivity with the anti-EE antibody on Western blots. Under these conditions, a small amount of cross-reactive material was also seen at 150,000 kDa.

Preparation of Anti-EE Sepharose

A 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.) and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was washed with 5 volumes of PBS containing 0.02% sodium azide and stored in this solution at 4° C.

EXAMPLE 8

Adhesion and Proliferation Assays

The ability of zsig37 to stimulate adhesion and spreading of TF-1 cells was assayed as follows. A series of dilutions were prepared from C-terminal Glu-Glu-tagged zsig37, from 10 to 0.0625 µg/ml, in either PBS or ELISA coating buffer (0.1 M $NaCO_3$) and each was plated into a 96 well plate (Costar, Pleasanton, Calif.) at 100 µl/well. The plates were incubated at 37° C., 5% $CO_2$ for 2 hours. The plates were then washed 3× with RPMI/10% FBS (RPMI 1640, 2 mM L-glutamine, 110 µg/ml sodium pyruvate, PSN and 10% heat inactivated fetal bovine serum) and allowed to block for 15 minutes.

TF-1 cells (derived from acute myeloid leukemia cells) were resuspended in RPMI/10% FBS and plated into at 10,000 cells/well into the zsig37CEE-coated 96 well plates at a final volume of 120 µl/well. The plate was incubated at 37° C. under 5% $CO_2$ for 2 hours. The plates were then washed 3×with PBS and 200 µl/well growth media (RPMI/ 10% FBS, 5 ng/ml GM-CSF) was added. The cells were microscopically inspected before and after the wash.

A dye incorporation assay was also used to quantitatively measure the number of adherent cells based on a colorimetric change and an increase in fluorescent signal. Alamar Blue™ (AccuMed, Chicago, Ill.) was added to the 96 well plates and the cells were incubated at 37° C. under 5% $CO_2$ overnight. The plates were then scanned using a fluorometer with excitation wavelength of 544 nm and emission wavelength of 590 nm. There were more adherent cells on the zsig37CEE-PBS coated plates than on the zsig37CEE-0.1 M $NaCO_3$ coated plates. Addition of soluble zsig37 did not block adhesion of cells to the bound zsig37.

A second assay was done using TF-1, DA-1 (an IL-3 dependent cell line derived from the lymph node of a mouse with a B-cell lymphoma by outgrowth in IL-3 media (provided by Dr. Kenneth Kaushansky, University of Washington, Seattle, Wash.)), pre-B (p53−/− mouse marrow cells, IL-7 dependent, B220+, Thy1 low, Sca-1+), and A7BaF-3 cell lines as described above at 5,000 cells/well. BHK cells were also plated at 500 cells/well. Zsig37 enhanced the growth of A7-BaF-3-cells and slightly inhibited growth of DA-1 cells.

EXAMPLE 9

Mouse Ortholog Sequence

The novel human zsig37 polypeptide-encoding polynucleotides of the present invention were used to screen a mouse EST database for homologous mouse sequences. A single EST sequence was discovered and predicted to the human zsig37 sequence. To identify the corresponding cDNA, a clone considered likely to contain the entire coding sequence was used for sequencing. Using an Invitrogen S.N.A.P.™ Miniprep kit (Invitrogen Corp.) according to manufacturer's instructions a 5 ml overnight culture in LB+50 µg/ml ampicillin was prepared. The template was sequenced on an ABIPRISM™ model 377 DNA sequencer (Perkin-Elmer Cetus, Norwalk, Conn.) using the ABI PRISM™ Big Dye Terminator Cycle Sequencing Ready Reaction Kit (Perkin-Elmer Corp.) according to manufacturer's instructions. Oligonucleotides ZC694 (SEQ ID NO:6), ZC6768 (SEQ ID NO:32), ZC18297 (SEQ ID NO:33), ZC18298 (SEQ ID NO:34), ZC18402 (SEQ ID NO:35), ZC18403 (SEQ ID NO:36), ZC18456 (SEQ ID NO:37), ZC18457 (SEQ ID NO:38), ZC18560 (SEQ ID NO:39), ZC18561 (SEQ ID NO:40), ZC18687 (SEQ ID NO:41) and ZC18688 (SEQ ID NO:42) were used to complete the sequence from the clone. Sequencing reactions were carried out in a Hybaid OmniGene Temperature Cycling System (National Labnet Co., Woodbridge, N.Y.). SEQUENCHER™ 3.1 sequence analysis software (Gene Codes Corporation, Ann Arbor, Mich.) was used for data analysis. The resulting 2559 bp sequence is disclosed in SEQ ID NO:43 and the deduced amino acid sequence in SEQ ID NO:44. Alignment with the human zsig37 nucleotide sequence (SEQ ID NO:1) shows 77% identity at the nucleotide level. The putative amino acid sequence (SEQ ID NO:44) has 77% identity with the human polypeptide sequence (SEQ ID NO:2).

EXAMPLE 10

Cell Based Assays

Zsig37 polypeptides were assayed in a high throughput, in vitro assay to identify substances that selectively activate cellular responses in immortalized osteoblast cell lines. A mature osteoblast cell line derived from p53−/− (deficient) mice, CCC4, that is transfected with a plasmid containing an inducible serum response element (SRE) driving the expression of luciferase was used in the assay. These cells also express endogenous PTH, PDGF and bFGF receptors. The stimulation of the SRE and thus the expression of luciferase in the CCC4 cells indicates that the chemical entity is likely to stimulate mitogenesis in osteoblasts.

CCC4 lines were trypsinized and adjusted to $5 \times 10^4$ cells/ ml in plating medium (alpha-MEM, 1% heat inactivated fetal bovine serum, 1 mM Na pyruvate and 2 mM L-glutamate) and plated (200 ul/well) into DYNATECH MICROLITE opaque white microtiter plates (Dynatech, Chantilly, VA) and incubated overnight at 37° C. 5% $CO_2$. The growth medium was then aspirated and replaced with 50 ul/well assay medium (F-12 HAM, 0.5% bovine serum albumin, 20 mM HEPES, 1 mM Na pyruvate and 2 mM L-glutamate). Serial dilutions of zsig37 were made in assay medium (0.29–1000 ng/ml final assay concentration) and added to the wells. Zsig37 samples were assayed in triplicate. Serum (negative) and bFGF (positive) controls were also used. Final concentration of bFGF was 3 ng/ml. Controls were assayed in quadruplicates. The plates were incubated for 4 hours at 37° C., 5% $CO_2$. The assay medium was then aspirated and the plates were rinsed once with PBS. To each well was then added 25 ml of lysis buffer (Luciferase Assay Reagent, E1501, Promega Corp., Madison, Wis.). The plates were incubated for 15 minutes at room temperature. Fifty microliters/well of luciferase substrate (Luciferase Assay Reagent, E 1501, Promega Corp.) was added and the Luciferase activity was detected using a Labsystems LUMINOSKAN®at 2 second/well following a 1 second delay. The average basal (uninduced) signal was subtracted from all readings which are expressed in Table 5 as a percentage of the maximal induction produced by 3 ng/ml bFGF.

Zsig37 stimulates the expression of luciferase in this assay indicating that they stimulate osteoblasts. Zsig37 stimulates at 73 to 75% maximal at 1000 ng/ml.

A counter part growth factor mimetic assay was performed to determine if zsig37 is acting as a growth factor mimetic, particularly tyrosine kinase receptor ligands PDGF, bFGF and EGF (Insulin-R negative). A clonal cell line derived from Swiss 3T3 mice, Swiss 3T3, that is transfected with a plasmid containing an inducible serum response element (SRE) driving the expression of luciferase was used in the assay. These cells also express endogenous PMA, EGF and BFGF receptors. The stimulation of the SRE and thus the expression of luciferase in the Swiss 3T3 cells indicates that the chemical entity is likely mimics the PDGF, bFGF and EGF growth factor activity.

Swiss 3T3 cells were trypsinized and adjusted to $5 \times 10^4$ cells/ml in plating medium, plated and incubated as described above. The growth medium was then aspirated and replaced with 50 ul/well assay medium (F-12 HAM, 0.5% bovine serum albumin, 20 mM HEPES). Serial dilutions of zsig37 were made in assay medium (0.29–1000 ng/ml final assay concentration) and added to the wells. Zsig37 samples were assayed in triplicate. A serum (negative) and bFGF (positive) control to promote cell proliferation were also used. Final concentration of bFGF was 3 ng/ml. Controls were assayed in quadruplicates. The plates were incubated for 5 hours at 37° C., 5% $CO_2$. The assay medium was then aspirated and the plates were rinsed once with PBS. To each well was then added 25 µl of lysis buffer (Luciferase Assay Reagent, E1501, Promega Corp., Madison, Wis.). The plates were incubated for 15 minutes at room temperature. Forty microliters/well of luciferase substrate (Luciferase Assay Reagent, E1501, Promega Corp.) was added and the Luciferase activity was detected using a Labsystems LUMINOSKAN® at 2 second/well following a 1 second delay. The average basal (uninduced) signal was subtracted from all readings which are expressed as a percentage of the maximal induction produced by 3 ng/ml bFGF. A five hour treatment of this cell line with bFGF, DDGF, EGF or PMA leads to a 25–50 fold induction of SRE-luciferase expression.

Zsig37 does not appear to stimulate the expression of luciferase in this assay. Zsig37 stimulates at 0.2 to 0.1% maximal at 1000 ng/ml.

Example 11

In vivo Administration of zsig37 Via Adenoviral Delivery

Twenty four male and 24 female C57B16/J mice, approximately 12 weeks old (Jackson Labs, Bar Harbor, Me.) were weighed, body temperature was measured and food intake monitored daily for four days prior to injection (days–4 to –1). On day 0, the mice were divided into three groups and received 0.1 ml virus (AdV-empty 1.8×1011 virus particles/ 0.1 ml or AdV-zsig37-CEE 5×1011 virus particles/0.1 ml) by intravenous tail vein injection, or no injection at all. Injection should result in infection of the host's liver and expression of virally delivered gene should commence within 24 hours and continue for 1 to 4 weeks. Three groups of mice were tested. Group 1, untreated, n=8 each male and female. Group 2, AdV-Empty (empty virus), n=8 each male and female. Group 3, AdV-zsig37 CEE, n=8 each male and female.

The animals' body temperatures, weights and the weight of food ingested was monitored during the three week study. No difference was found between the groups.

On day 21 the female mice were euthanized and sacrificed by cervical dislocation, and on day 22 the males were. The animals were exsanguinated and tissues harvested for necropsy.

The standard serum chemistry panel was done at the time of sacrifice. Liver, kidney and metabolic parameters were all within normal ranges. There was, however a difference between the zsig37 treatment group and the empty virus treated group. The zsig37 animals had a higher average lipemic index than the empty virus controls. The difference was not significant, however further investigation was warranted. Total free fatty acids were assayed on the remaining serum from each animal. A statistically significant difference in serum Free Fatty Acid levels was seen between male mice (p=0.0379) receiving empty virus and those receiving zsig37 encoding virus; the zsig37 mice had higher levels. A difference, though not statistically significant, was also seen in females (p=0.3357). Liver, spleen, kidney, thymus, heart and brain were weighed after removal. No difference was found between the treatment groups. Histopathological analysis of these tissues and bone marrow revealed no difference between the treatment groups.

To confirm the above results a second screen was done as above with the following modifications. Three groups; a) untreated and fasted, b) AdV-null and fasted, c) AdV-zsig37-CEE and fasted, containing 20 C57B16/J, 10 each male and female, were tested. The mice were fasted overnight and 100 µl serum was collected to establish a basal level for the following parameters: fasting glucose, TP, alkaline phosphatase, cholesterol, triglycerides, free fatty acids and insulin. Body weights were taken three times a week. On day 0, mice were injected into the lateral tail vein with 0.1 ml of the appropriate virus solution. Blood was collected on day 17 following an overnight fast. After 3 weeks the mice were sacrificed and all blood collected. A portion of the blood was mixed with EDTA to look at CBC's and the remainder will be re-assayed and screened as described above. Organs were collected and the carcass saved for histopathology.

EXAMPLE 11

SEC-MALLS Analysis of Zsiq37

Zsig37 contains a N-terminal collagen-like domain as well as a C-terminal globular region having homology to the tumor necrosis factor family and like other such proteins, zsig37 is expected to multimerize. Purified zsig37 analyzed using an ESI-ion trap mass spectrometer (Finnigan-MAT LCQ, San Jose, Calif.) indicated the presence of species approximating trimers and 9mers, which was an unexpected result when compared to other homologous proteins. Peptide mapping of zsig37 using LC-MS/MS on an ESI-ion trap mass spectrometer (Finnigan-MAT LCQ) revealed that several cysteine residues were modified with an S-cysteinyl group. It may be that modification of key cysteine residues in the zsig37 protein during fermentation with free cysteine in the media is preventing proper oliomeric association of this molecule.

To learn more, a comparison of reduced and non-reduces zsig37 was made using a Biosep S-3000 size exclusion column at 1.0 ml/minute (7.8×3000 mm; Phenomenex, Torrance Calif.) on a HP 1050 HPLC (Hewlett Packard, Heidelberg, Germany). The HP 1050 was coupled to light scattering and refractive index detectors, miniDAWN and Optilab DSP, Wyatt Technology, Santa Barbara, Calif.) for on-line SEC-MALLS.

One milligram of recombinant zsig37 (1.0 mg/ml) was added to TCEP at a 10:1 mol/mol ratio of TCEP to zsig37 and at kept at room temperature for 70 minutes. Sixty microliters of the reduced zsig37 was injected for SEC-MALLS analysis and the remainder of the reduced zsig37 was dialyzed in 0.5–3.0 ml SLIDE-A-LYZER cassettes, 10K MWCO (Pierce, Rockford, Ill.) with stirring against PBS, pH 7.4 with three buffer changes as follows: 1 liter PBS at room temperature for 4 hours, 1 liter PBS at 4° C. overnight, and 1 liter PBS at room temperature for 4 hours.

Following dialysis, oxidation was allowed to continue at 4° C. The oxidation was monitored by SEC-MALLS analysis of aliquotes taken at three time points, T=0, T=24 hours and T=96 hours. Molecular weight values were determined using the LS-RI, two-detector method.

Analysis of the reduced, dialyzed recombinant zsig37 seems to initially indicate the formation of hexamers and 18mers as detected by SEC-MALLS which is more consistent with the oligomeric states observed in homologs. These forms were also active in in vitro assays.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide consisting of a sequence of amino acid residues that is at least 95% identical in amino acid sequence to amino acid residues 26 to 281 of SEQ ID NO:2, wherein the amino acid sequence comprises (1) Gly-Xaa-Xaa or Gly-Xaa-Pro repeats forming a collagen domain, wherein Xaa is any amino acid, and (2) a carboxy-terminal globular portion, and wherein a characteristic of the polypeptide is stimulation of acute myeloid leukemia cell TF-1) adhesion.

2. The isolated polypeptide of claim 1 wherein any differences between the polypeptide and the polypeptide of SEQ ID NO:2 are due to conservative amino acid substitutions.

3. The isolated polypeptide of claim 1 wherein the collagen domain consists of 13 Gly-Xaa-Xaa repeats and 1 Gly-Xaa-Pro repeat.

4. The isolated polypeptide of claim 1 wherein the globular domain consists of ten beta sheets.

5. The isolated polypeptide of claim 4 wherein the beta sheets are associated with amino acid residues corresponding to amino acid residues 147 to 151 of SEQ ID NO:2, amino acid residues 170 to 172 of SEQ ID NO:2, amino acid residues 178 to 181 of SEQ ID NO:2, amino acid residues 185 to 188 of SEQ ID NO:2, amino acid residues 191 to 203 of SEQ ID NO:2, amino acid residues 207 to 214 of SEQ ID NO:2, amino acid residues 219 to 225 of SEQ ID NO:2, amino acid residues 227 to 238 of SEQ ID NO:2, amino acid residues 244 to 250 of SEQ ID NO:2, and amino acid residues 269 to 274 of SEQ ID NO:2.

6. A polypeptide oligomer comprising at least two polypeptides of claim 1.

7. The polypeptide oligomer of claim 6 wherein the polypeptides are linked by intermolecular disulfide bonds.

8. The polypeptide oligomer of claim 6 wherein the oligomer is a trimer.

9. The polypeptide oligomer of claim 6 wherein the oligomer is a hexamer.

10. The polypeptide oligomer of claim 6 wherein the oligomer is an 18mer.

11. The isolated polypeptide of claim 1 wherein the polypeptide is covalently linked amino terminally or carboxy terminally to a moiety selected from the group consisting of affinity tags, toxins, radionucleotides, enzymes and fluorophores.

12. The isolated polypeptide of claim 11 further comprising a proteolytic cleavage site between said sequence of amino acid residues and said affinity tag.

13. An isolated polypeptide comprising a sequence of amino acid residues that is at least 95% identical in amino acid sequence to amino acid residues 26 to 281 of SEQ ID NO:2, wherein the amino acid sequence comprises (I) Gly-Xaa-Xaa or Gly-Xaa-Pro repeats forming a collagen domain, wherein Xaa is any amino acid, and (2) a carboxy-terminal globular portion, and wherein a characteristic of the polypeptide is stimulation of acute myeloid leukemia cell (TF-1) adhesion.

14. The isolated polypeptide of claim 13 wherein any differences between the polypeptide and the polypeptide of SEQ ID NO:2 are due to conservative amino acid substitutions.

15. The isolated polypeptide of claim 13 wherein the collagen domain consists of 13 Gly-Xaa-Xaa repeats and 1 Gly-Xaa-Pro repeat.

16. The isolated polypeptide of claim 13 wherein the globular domain consists of ten beta sheets.

17. The isolated polypeptide of claim 16 wherein the beta sheets are associated with amino acid residues corresponding to amino acid residues 147 to 151 of SEQ ID NO:2, amino acid residues 170 to 172 of SEQ ID NO:2, amino acid residues 178 to 181 of SEQ ID NO:2, amino acid residues 185 to 188 of SEQ ID NO:2, amino acid residues 191 to 203 of SEQ ID NO:2, amino acid residues 207 to 214 of SEQ ID NO:2, amino acid residues 219 to 225 of SEQ ID NO:2, amino acid residues 227 to 238 of SEQ ID NO:2, amino acid residues 244 to 250 of SEQ ID NO:2, and amino acid residues 269 to 274 of SEQ ID NO:2.

18. A polypeptide oligomer comprising at least two polypeptides of claim 13.

19. The polypeptide oligomer of claim 18 wherein the polypeptides are linked by intermolecular disulfide bonds.

20. The polypeptide oligomer of claim 18 wherein the oligomer is a trimer.

21. The polypeptide oligomer of claim 18 wherein the oligomer is a hexamer.

22. The polypeptide oligomer of claim 18 wherein the oligomer is an 18mer.

23. The isolated polypeptide of claim 13 wherein the polypeptide is covalently linked amino terminally or carboxy terminally to a moiety selected from the group consisting of affinity tags, toxins, radionucleotides, enzymes and fluorophores.

24. The isolated polypeptide of claim 23 further comprising a proteolytic cleavage site between said sequence of amino acid residues and said affinity tag.

* * * * *